US009428755B2

(12) United States Patent
Reeves

(10) Patent No.: US 9,428,755 B2
(45) Date of Patent: Aug. 30, 2016

(54) USE OF CLOSTRIDIAL METHYLTRANSFERASES FOR GENERATING NOVEL STRAINS

(71) Applicant: Coskata, Inc., Warrenville, IL (US)

(72) Inventor: Andrew Reeves, Chicago, IL (US)

(*) Notice: Subject to any disclaimer, the term of this patent is extended or adjusted under 35 U.S.C. 154(b) by 0 days.

(21) Appl. No.: 14/592,208

(22) Filed: Jan. 8, 2015

(65) Prior Publication Data

US 2015/0191736 A1    Jul. 9, 2015

Related U.S. Application Data

(63) Continuation of application No. 14/209,634, filed on Mar. 13, 2014, now Pat. No. 9,045,758.

(60) Provisional application No. 61/780,731, filed on Mar. 13, 2013.

(51) Int. Cl.
| | | |
|---|---|---|
| *C12N 15/74* | (2006.01) | |
| *C12N 15/63* | (2006.01) | |
| *C12N 9/10* | (2006.01) | |
| C12N 15/70 | (2006.01) | |
| C12N 15/87 | (2006.01) | |

(52) U.S. Cl.
CPC ............. *C12N 15/74* (2013.01); *C12N 9/1007* (2013.01); *C12N 15/63* (2013.01); *C12N 15/70* (2013.01); *C12N 15/87* (2013.01); *C12Q 2521/331* (2013.01); *C12Y 201/01072* (2013.01)

(58) Field of Classification Search
None
See application file for complete search history.

(56) References Cited

U.S. PATENT DOCUMENTS

| | | |
|---|---|---|
| 7,820,408 B2 | 10/2010 | Thomas et al. |
| 2011/0229947 A1 | 9/2011 | Zahn et al. |
| 2011/0236941 A1 | 9/2011 | Koepke et al. |
| 2012/0270297 A1 | 10/2012 | Xu et al. |

FOREIGN PATENT DOCUMENTS

| | | |
|---|---|---|
| WO | WO2008028055 | 3/2008 |
| WO | WO2009137778 A2 | 11/2009 |
| WO | WO2012105853 A1 | 8/2012 |

OTHER PUBLICATIONS

Mermelstein et al., 1993, Applied and Environmental Microbiology, 59:1077-1081.
Allen and Blaschek, 1990, FEMS Microbiology Letters, 58:217.
de Feyter et al., 1991, Journal of Bacteriology, 173:6421-6427.
Mann et al., 1978, Gene 3:97-102.
Kennaway et al., 2009, Nucleic Acids Research, 37(3):762-770.
Antoine and Locht., 1992, Mol. Microbiol. 6(13): 1785-1799.
Abrini J, et al., 1994, Arch. Microbiol. , 4:345-351.
Weisblum et al., 1979, Journal of Bacteriology, p. E194, 137:635-643.
Parke D, 1990, Gene, 93(1): 135-137.
Leang, et al., 2012, Applied and Environmental Microbiology, Epub ahead of print Nov. 30, 2012.
NCBI , NCBI Reference Sequence No: WP_001064588.1, Feb. 5, 2013 1 page.
Suzuki, 2012, InTech, Host-mimicking strategies in DNA methylation for improved bacterial transformation in Methyulation—from DNA, RNA and histones to diseases and treatment, 219-236.
International Search Report for International application No. PCT/US2014/026350, mailed Sep. 1, 2014. 5 pages.
Written Opinion for International application No. PCT/US2014/026350, mailed Sep. 1, 2014. 6 pages.

*Primary Examiner* — Catherine S Hibbert
*Assistant Examiner* — Channing S Mahatan
(74) *Attorney, Agent, or Firm* — McDonnell Boehnen Hulbert & Berghoff LLP

(57) ABSTRACT

This invention provides isolated polynucleotides encoding DNA Type I methyltransferase and uses thereof for improving transformation efficiencies of exogenous and endogenous plasmid DNA into Clostridial hosts.

12 Claims, 11 Drawing Sheets

Fig. 1A.

ATGAATACACAGGAAATAGTAAGCAAACTTTGGAACCTTTGTAACGTACTAA
GAGATGATGGAATAACTTATCATCAATATGTAACAGAATTAACATATATTCTT
TTCTTAAAGATGGCAAAGGAAACAGGTACAGAGGATAAATTGCCAGAAGGTT
ATAGATGGGATGATTTAAAAGTTTATAGAGGAATGGAACTTAAGAAATTTTA
TAATAAATTATTAAATTATCTTGGAGAAAAGACTACTGGGATAGTGCAAAAA
ATATATCAGGGATCTGCAACAAATATAGAAGAACCAAAAAATCTAGAAAAA
ATAATTAAAACTATAGATGGATTAGATTGGTATTCAGCAAAAGAAGAAGGAC
TTGGAAACTTATATGAAGGATTACTTGAAAAAAATGCATCTGAGAAAAAATC
TGGTGCAGGACAATACTTTACTCCAAGAGTATTAATTAATGTTATGGTGGAAC
TTATTGATCCAAAACCAGGTGAAAAATGCAATGACCCTGCAGCAGGAACCTT
TGGATTTATGATTGCTGCAGATCGTTACATGAAACAGAAAACAGACAACTAT
TTTGATTTAGGTACAGAACTTCAAGAGTTTCAGAGAACTAAGGCTTTTTCTGG
CTGTGAATTAGTTCACGAAACACATAGATTAGCCCTTATGAATGCTATGCTTC
ATGATATAGAAGGAAACATAATCCTCGGAGATACTTTAACAAATACAGGAAA
GCAGATGAAAGACTTAAATGTTGTGCTTTCAAACCCTCCATTTGGAACTAAA
AGAGGTGGTGAAAGAGCAACAAGAGATGATTTGACTTACATGACTTCAAATA
AACAATTAAACTTCTTGCAGCACATATATAGAAGTTTAAAAGCAGATGGAAA
AGCAAGAGCAGCTGTGGTATTGCCAGATAATGTACTATTTGATCATAATGAT
GGAGCGAAGATTCGTGCGGATTTAATGGATAAATGTAATCTACATACAATAT
TACGGTTACCTACTGGTATTTTCTATGCTAAAGGAGTTAAAACAAATGTGCTT
TTCTTTACTAGAGGTACTAGTGATAAAGACAATACTAAAGAAGTTTGGATAT
ATGATTTGCGTACCAATATGCCTAGCTTTGGAAAGACAAATCCTTTAAAGAA
AGAGCATTTTGAAGACTTTATAAAGGCTTATACTTCTGAGGATAGAACAAAG
GTGAAAGATGAACGTTTTTCGGTATTTACTAGAGAAGAAATAAAAGAGAAAA
ATGATAACCTTGACCTAGGTTTAATTCGTGATGAAAGTGTATTAGACTATGAA
GATCTACAAGATCCAATTGAAAGTGGTGAAGAAATAACTTCACAACTTGAAG
AGGCAATGGATTTAATCCAAACTGTTGTAAAGAAACTAAAGATTTTAGGCGG
TGACAGGTAA [SEQ ID NO: 1]

Fig. 1B

```
MNTQEIVSKLWNLCNVLRDDGITYHQYVTELTYI
LFLKMAKETGTEDKLPEGYRWDDLKVYRGMELK
KFYNKLLNYLGEKTTGIVQKIYQGSATNIEEPKN
LEKIIKTIDGLDWYSAKEEGLGNLYEGLLEKNAS
EKKSGAGQYFTPRVLINVMVELIDPKPGEKCNDP
AAGTFGFMIAADRYMKQKTDNYFDLGTELQEFQ
RTKAFSGCELVHETHRLALMNAMLHDIEGNIILG
DTLTNTGKQMKDLNVVLSNPPFGTKRGGERATR
DDLTYMTSNKQLNFLQHIYRSLKADGKARAAVV
LPDNVLFDHNDGAKIRADLMDKCNLHTILRLPTG
IFYAKGVKTNVLFFTRGTSDKDNTKEVWIYDLRT
NMPSFGKTNPLKKEHFEDFIKAYTSEDRTKVKDE
RFSVFTREEIKEKNDNLDLGLIRDESVLDYEDLQ
DPIESGEEITSQLEEAMDLIQTVVKKLKILGGDR
```

[SEQ ID NO: 2]

Fig. 2A

ATGTCAATAACAAACGTAGTAAAATCAGTACAAGATATAATGCGCCAGGATGCAGG
GGTAGATGGAGATGCTCAAAGAATATCTCAACTAGTTTGGATGATATTTTTAAAGGT
ATTTGATGCAAAAGAAGAGGAATGGGAATTAGAGTATGATGATTATACACCTATTA
TTCCAGAAGAATTGAGATGGAGCAACTGGGCTCAAGATGATGAAGGAATTACAGGC
GATGAGCTTTTAGACTTTGTAAACAATAAATTATTCAAAGGTTTAAAGGAAATGGAA
GTAGATGAGAATAGTGATGCTAAAGCTTTATTAGTTAAATCTGTATTTGAAGATTCC
TATAATTATATGAAATCAGGAGCTTTAATGAGGCAGGTAATAAATAAGTTAAATGA
AATAGATTTTACAGCAGGTGAAGACAGACATTTATTTAATGATATATATGAAAATAT
ATTAAAAGATCTTCAAAGTGCAGGCAATGCAGGAGAATTCTATACACCAAGACCTG
TTACACAATTTATAATAGATATGCTAAGTCCAAAGCTTGGTGAAAAAGTAGCTGACT
TTGCTTGTGGTACCGGTGGATTTTTAACATGTGCCATAGAAAACTTAAAAAAACAGG
AAACCAAAGTTGAAGATTTAAAAATATTAGGTGAAACCATAATGGGTGTAGAAAAG
AAACCGCTTCCTCACATGCTTGCTACAACTAACCTGATACTTCATGATATTGATGTGC
CAAACATAAAACATGATAATTCTTTGATGAAGAATGTAAGAGATTTAAAGCCTTCAG
AATATGTGGATGTAATAGCAATGAATCCTCCTTTTGGCGGAATTGAAGAAGATATGG
TACTAACTAATTTCCCTCAGCAGTTTCAAACAAAAGAAACAGCAGATTTATTTATGA
CTCTTATAATGTATAGATTAAGTGAAAAAGGAAGAGCGGGAGTAGTACTTCCAGAT
GGATTTTTATTTGGTGAAGGTGTAAAGACTCATATAAAAGAAAAACTTTTAAATGAA
TTTAACCTTCATACTATAGTAAGAATGCCTAATGGAGTATTTGCCCCATATACGGGA
ATAAATACAAACCTTTTATTCTTTGAAAAAGGTAAGCCAACAGAAGAAGTTTGGTTC
TTTGAACATCCACTTCCTGAAGGATATAAAAATTATACTAAAACCAAACCAATAAGA
TATGAAGAATTTGAACTGGAGAAGAAGTGGTGGAATAACAGAGAAGAAAATGAGT
ATGCGTGGAAGGTTTCAGTAGAGGACATTAAAAATAGAAATTATAATTTAGATTATA
AAAATCCTAATAAGGAAGAAGAAGATTTAGGAGATCCAAAGGCATTATTAAAAAAA
TATCATGAAGCTGCTGCTGATGTAGATAAATTGCAAGATTCTTTGATAGATGAATTA
AAGAAGATTTTAGAAGGGACATCAAAATAG [SEQ ID NO: 3]

Fig. 2B

MSITNVVKSVQDIMRQDAGVDGDAQRISQLVWM
IFLKVFDAKEEEWELEYDDYTPIIPEELRWSNWA
QDDEGITGDELLDFVNNKLFKGLKEMEVDENSD
AKALLVKSVFEDSYNYMKSGALMRQVINKLNEI
DFTAGEDRHLFNDIYENILKDLQSAGNAGEFYTP
RPVTQFIIDMLSPKLGEKVADFACGTGGFLTCAI
ENLKKQETKVEDLKILGETIMGVEKKPLPHMLAT
TNLILHDIDVPNIKHDNSLMKNVRDLKPSEYVDV
IAMNPPFGGIEEDMVLTNFPQQFQTKETADLFMT
LIMYRLSEKGRAGVVLPDGFLFGEGVKTHIKEKL
LNEFNLHTIVRMPNGVFAPYTGINTNLLFFEKGK
PTEEVWFFEHPLPEGYKNYTKTKPIRYEEFELEK
KWWNNREENEYAWKVSVEDIKNRNYNLDYKNP
NKEEEDLGDPKALLKKYHEAAADVDKLQDSLID
ELKKILEGTSK [SEQ ID NO: 4]

Fig. 3

TGATTGATTATTTATTTTAAAATGCCTAAGTGAAATATATACATATTATAACAATAA
AATAAGTATTAGTGTAGGATTTTTAAATAGAGTATCTATTTTCAGATTAAATTTTTGA
TTATTTGATTTACATTATATAATATTGAGTAAAGTATTGACTAGCAAAATTTTTTGAT
ACTTTAATTTGTGAAATTTCTTATCAAAAGTTATATTTTTGAATAATTTTTATTGAAA
AATACAACTAAAAAGGATTATAGTATAAGTGTGTGTAATTTTGTGTTAAATTTAAAG
GGAGGAAAATGTCAATAACAAACGTAGTAAAATCAGTACAAGATATAATGCGCCAG
GATGCAGGGGTAGATGGAGATGCTCAAAGAATATCTCAACTAGTTTGGATGATATTT
TTAAAGGTATTTGATGCAAAAGAAGAGGAATGGGAATTAGAGTATGATGATTATAC
ACCTATTATTCCAGAAGAATTGAGATGGAGCAACTGGGCTCAAGATGATGAAGGAA
TTACAGGCGATGAGCTTTTAGACTTTGTAAACAATAAATTATTCAAAGGTTTAAAGG
AAATGGAAGTAGATGAGAATAGTGATGCTAAAGCTTTATTAGTTAAATCTGTATTTG
AAGATTCCTATAATTATATGAAATCAGGAGCTTTAATGAGGCAGGTAATAAATAAGT
TAAATGAAATAGATTTTACAGCAGGTGAAGACAGACATTTATTTAATGATATATATG
AAAATATATTAAAAGATCTTCAAAGTGCAGGCAATGCAGGAGAATTCTATACACCA
AGACCTGTTACACAATTTATAATAGATATGCTAAGTCCAAAGCTTGGTGAAAAAGTA
GCTGACTTTGCTTGTGGTACCGGTGGATTTTTAACATGTGCCATAGAAAACTTAAAA
AAACAGGAAACCAAAGTTGAAGATTTAAAAATATTAGGTGAAACCATAATGGGTGT

Fig 3 (cont.)

AGAAAAGAAACCGCTTCCTCACATGCTTGCTACAACTAACCTGATACTTCATGATAT
TGATGTGCCAAACATAAAACATGATAATTCTTTGATGAAGAATGTAAGAGATTTAAA
GCCTTCAGAATATGTGGATGTAATAGCAATGAATCCTCCTTTTGGCGGAATTGAAGA
AGATATGGTACTAACTAATTTCCCTCAGCAGTTTCAAACAAAAGAAACAGCAGATTT
ATTTATGACTCTTATAATGTATAGATTAAGTGAAAAGGAAGAGCGGGAGTAGTAC
TTCCAGATGGATTTTTATTTGGTGAAGGTGTAAAGACTCATATAAAAGAAAAACTTT
TAAATGAATTTAACCTTCATACTATAGTAAGAATGCCTAATGGAGTATTTGCCCCAT
ATACGGGAATAAATACAAACCTTTTATTCTTTGAAAAAGGTAAGCCAACAGAAGAA
GTTTGGTTCTTTGAACATCCACTTCCTGAAGGATATAAAAATTATACTAAAACCAAA
CCAATAAGATATGAAGAATTTGAACTGGAGAAGAAGTGGTGGAATAACAGAGAAG
AAAATGAGTATGCGTGGAAGGTTTCAGTAGAGGACATTAAAAATAGAAATTATAAT
TTAGATTATAAAAATCCTAATAAGGAAGAAGAAGATTTAGGAGATCCAAAGGCATT
ATTAAAAAAATATCATGAAGCTGCTGCTGATGTAGATAAATTGCAAGATTCTTTGAT
AGATGAATTAAAGAAGATTTTAGAAGGGACATCAAAATAGTATGGAAATGTTATTA
GAACAATTTAAAATAATATTTGATAGACCAGAAAAAGTTAAGAGATTGAGAGATTT
AATACTACAGTTAGCGGTAAGGGGAAAGTTAGTAGAGCAGGATGAAAACGATGAGC
CAGCCAGTGTGCTTTTGGAGAGAATAAAAGAAGAAAGAGAGAAGCTCATTAAAGAA
GGAAAGATAAAGAACGCGTTTGTTTAAAGGGAGGAAAATGAATACACAGGAAATA
GTAAGCAAACTTTGGAACCTTTGTAACGTACTAAGAGATGATGGAATAACTTATCAT
CAATATGTAACAGAATTAACATATATTCTTTTCTTAAAGATGGCAAAGGAAACAGGT
ACAGAGGATAAATTGCCAGAAGGTTATAGATGGGATGATTTAAAAGTTTATAGAGG
AATGGAACTTAAGAAATTTTATAATAAATTATTAAATTATCTTGGAGAAAAGACTAC
TGGGATAGTGCAAAAAATATATCAGGGATCTGCAACAAATATAGAAGAACCAAAAA
ATCTAGAAAAAATAATTAAAACTATAGATGGATTAGATTGGTATTCAGCAAAAGAA
GAAGGACTTGGAAACTTATATGAAGGATTACTTGAAAAAAATGCATCTGAGAAAAA
ATCTGGTGCAGGACAATACTTTACTCCAAGAGTATTAATTAATGTTATGGTGGAACT
TATTGATCCAAAACCAGGTGAAAAATGCAATGACCCTGCAGCAGGAACCTTTGGAT
TTATGATTGCTGCAGATCGTTACATGAAACAGAAAACAGACAACTATTTTGATTTAG
GTACAGAACTTCAAGAGTTTCAGAGAACTAAGGCTTTTTCTGGCTGTGAATTAGTTC
ACGAAACACATAGATTAGCCCTTATGAATGCTATGCTTCATGATATAGAAGGAAAC
ATAATCCTCGGAGATACTTTAACAAATACAGGAAAGCAGATGAAAGACTTAAATGT
TGTGCTTTCAAACCCTCCATTTGGAACTAAAAGAGGTGGTGAAAGAGCAACAAGAG
ATGATTTGACTTACATGACTTCAAATAAACAATTAAACTTCTTGCAGCACATATATA
GAAGTTTAAAAGCAGATGGAAAAGCAAGAGCAGCTGTGGTATTGCCAGATAATGTA
CTATTTGATCATAATGATGGAGCGAAGATTCGTGCGGATTTAATGGATAAATGTAAT
CTACATACAATATTACGGTTACCTACTGGTATTTTCTATGCTAAAGGAGTTAAAACA
AATGTGCTTTTCTTTACTAGAGGTACTAGTGATAAAGACAATACTAAAGAAGTTTGG
ATATATGATTTGCGTACCAATATGCCTAGCTTTGGAAAGACAAATCCTTTAAAGAAA
GAGCATTTTGAAGACTTTATAAAGGCTTATACTTCTGAGGATAGAACAAAGGTGAA
AGATGAACGTTTTTCGGTATTTACTAGAGAAGAAATAAAAGAGAAAAATGATAACC
TTGACCTAGGTTTAATTCGTGATGAAAGTGTATTAGACTATGAAGATCTACAAGATC
CAATTGAAAGTGGTGAAGAAATAACTTCACAACTTGAAGAGGCAATGGATTTAATC
CAAACTGTTGTAAAGAAACTAAAGATTTTAGGCGGTGACAGGTAA [SEQ ID NO: 9]

__NUM__US 9,428,755 B2__NUM__

SEQUENCE LISTING

<160> NUMBER OF SEQ ID NOS: 11

<210> SEQ ID NO 1
<211> LENGTH: 1419
<212> TYPE: DNA
<213> ORGANISM: Artificial Sequence
<220> FEATURE:
<223> OTHER INFORMATION: Polynucleotide sequence of MtaseI-1

<400> SEQUENCE: 1

```
atgaatacac aggaaatagt aagcaaactt tggaaccttt gtaacgtact aagagatgat      60
ggataacttt atcatcaata tgtaacagaa ttaacatata ttcttttctt aaagatggca     120
aaggaaacag gtacagagga taaattgcca gaaggttata gatgggatga tttaaaagtt     180
tatagaggaa tggaacttaa gaatttttat aataaattat taaattatct tggagaaaag     240
actactggga tagtgcaaaa aatatatcag ggatctgcaa caaatataga agaaccaaaa     300
aatctagaaa aaataattaa aactatagat ggattagatt ggtattcagc aaaagaagaa     360
ggacttggaa acttatatga aggattactt gaaaaaaatg catctgagaa aaaatctggt     420
gcaggacaat actttactcc aagagtatta attaatgtta tggtggaact tattgatcca     480
aaaccaggtg aaaaatgcaa tgaccctgca gcaggaacct ttggatttat gattgctgca     540
gatcgttaca tgaaacagaa aacagacaac tattttgatt taggtacaga acttcaagag     600
tttcagagaa ctaaggcttt ttctggctgt gaattagttc acgaaacaca tagattagcc     660
cttatgaatg ctatgcttca tgatatagaa ggaaacataa tcctcggaga tactttaaca     720
aatacaggaa agcagatgaa agacttaaat gttgtgcttt caaaccctcc atttggaact     780
```

```
aaaagaggtg gtgaaagagc aacaagagat gatttgactt acatgacttc aaataaacaa     840
ttaaacttct tgcagcacat atatagaagt ttaaaagcag atggaaaagc aagagcagct     900
gtggtattgc cagataatgt actatttgat cataatgatg gagcgaagat tcgtgcggat     960
ttaatggata aatgtaatct acatacaata ttacggttac ctactggtat tttctatgct    1020
aaaggagtta aaacaaatgt gcttttcttt actagaggta ctagtgataa agacaatact    1080
aaagaagttt ggatatatga tttgcgtacc aatatgccta gctttggaaa gacaaatcct    1140
ttaaagaaag agcattttga agactttata aaggcttata cttctgagga tagaacaaag    1200
gtgaaagatg aacgtttttc ggtatttact agagaagaaa taaaagagaa aaatgataac    1260
cttgacctag gtttaattcg tgatgaaagt gtattagact atgaagatct acaagatcca    1320
attgaaagtg gtgaagaaat aacttcacaa cttgaagagg caatggattt aatccaaact    1380
gttgtaaaga aactaaagat tttaggcggt gacaggtaa                           1419
```

<210> SEQ ID NO 2
<211> LENGTH: 472
<212> TYPE: PRT
<213> ORGANISM: Artificial Sequence
<220> FEATURE:
<223> OTHER INFORMATION: Amino acid sequence of MtaseI-1

<400> SEQUENCE: 2

```
Met Asn Thr Gln Glu Ile Val Ser Lys Leu Trp Asn Leu Cys Asn Val
1               5                   10                  15

Leu Arg Asp Asp Gly Ile Thr Tyr His Gln Tyr Val Thr Glu Leu Thr
            20                  25                  30

Tyr Ile Leu Phe Leu Lys Met Ala Lys Glu Thr Gly Thr Glu Asp Lys
        35                  40                  45

Leu Pro Glu Gly Tyr Arg Trp Asp Asp Leu Lys Val Tyr Arg Gly Met
    50                  55                  60

Glu Leu Lys Lys Phe Tyr Asn Lys Leu Leu Asn Tyr Leu Gly Glu Lys
65                  70                  75                  80

Thr Thr Gly Ile Val Gln Lys Ile Tyr Gln Gly Ser Ala Thr Asn Ile
                85                  90                  95

Glu Glu Pro Lys Asn Leu Glu Lys Ile Ile Lys Thr Ile Asp Gly Leu
            100                 105                 110

Asp Trp Tyr Ser Ala Lys Glu Glu Gly Leu Gly Asn Leu Tyr Glu Gly
        115                 120                 125

Leu Leu Glu Lys Asn Ala Ser Glu Lys Lys Ser Gly Ala Gly Gln Tyr
    130                 135                 140

Phe Thr Pro Arg Val Leu Ile Asn Val Met Val Glu Leu Ile Asp Pro
145                 150                 155                 160

Lys Pro Gly Glu Lys Cys Asn Asp Pro Ala Ala Gly Thr Phe Gly Phe
                165                 170                 175

Met Ile Ala Ala Asp Arg Tyr Met Lys Gln Lys Thr Asp Asn Tyr Phe
            180                 185                 190

Asp Leu Gly Thr Glu Leu Gln Glu Phe Gln Arg Thr Lys Ala Phe Ser
        195                 200                 205

Gly Cys Glu Leu Val His Glu Thr His Arg Leu Ala Leu Met Asn Ala
    210                 215                 220

Met Leu His Asp Ile Glu Gly Asn Ile Ile Leu Gly Asp Thr Leu Thr
225                 230                 235                 240

Asn Thr Gly Lys Gln Met Lys Asp Leu Asn Val Val Leu Ser Asn Pro
                245                 250                 255
```

```
Pro Phe Gly Thr Lys Arg Gly Gly Glu Arg Ala Thr Arg Asp Asp Leu
                260                 265                 270

Thr Tyr Met Thr Ser Asn Lys Gln Leu Asn Phe Leu Gln His Ile Tyr
            275                 280                 285

Arg Ser Leu Lys Ala Asp Gly Lys Ala Arg Ala Val Val Leu Pro
        290                 295                 300

Asp Asn Val Leu Phe Asp His Asn Asp Gly Ala Lys Ile Arg Ala Asp
305                 310                 315                 320

Leu Met Asp Lys Cys Asn Leu His Thr Ile Leu Arg Leu Pro Thr Gly
                325                 330                 335

Ile Phe Tyr Ala Lys Gly Val Lys Thr Asn Val Leu Phe Phe Thr Arg
            340                 345                 350

Gly Thr Ser Asp Lys Asp Asn Thr Lys Glu Val Trp Ile Tyr Asp Leu
        355                 360                 365

Arg Thr Asn Met Pro Ser Phe Gly Lys Thr Asn Pro Leu Lys Lys Glu
    370                 375                 380

His Phe Glu Asp Phe Ile Lys Ala Tyr Thr Ser Glu Asp Arg Thr Lys
385                 390                 395                 400

Val Lys Asp Glu Arg Phe Ser Val Phe Thr Arg Glu Glu Ile Lys Glu
                405                 410                 415

Lys Asn Asp Asn Leu Asp Leu Gly Leu Ile Arg Asp Glu Ser Val Leu
            420                 425                 430

Asp Tyr Glu Asp Leu Gln Asp Pro Ile Glu Ser Gly Glu Glu Ile Thr
        435                 440                 445

Ser Gln Leu Glu Glu Ala Met Asp Leu Ile Gln Thr Val Val Lys Lys
    450                 455                 460

Leu Lys Ile Leu Gly Gly Asp Arg
465                 470

<210> SEQ ID NO 3
<211> LENGTH: 1446
<212> TYPE: DNA
<213> ORGANISM: Artificial Sequence
<220> FEATURE:
<223> OTHER INFORMATION: Polynucleotide sequence of Mtase I-2

<400> SEQUENCE: 3
atgtcaataa caaacgtagt aaaatcagta caagatataa tgcgccagga tgcaggggta        60
gatggagatg ctcaaagaat atctcaacta gtttggatga tattttttaa ggtatttgat       120
gcaaaagaag aggaatggga attagagtat gatgattata cacctattat tccagaagaa       180
ttgagatgga gcaactgggc tcaagatgat gaaggaatta caggcgatga gcttttagac       240
tttgtaaaca ataaattatt caaaggttta aggaaatgga agtagatga gaatagtgat        300 gctaaagctt tattagttaa atctgtattt gaagattcct ataattatat gaaatcagga       360
gctttaatga ggcaggtaat aaataagtta atgaaatag attttacagc aggtgaagac       420
agacatttat ttaatgatat atatgaaaat atattaaaag atcttcaaag tgcaggcaat       480
gcaggagaat tctatacacc aagacctgtt acacaattta taatagatat gctaagtcca       540
aagcttggtg aaaagtagc tgactttgct tgtggtaccg gtggattttt aacatgtgcc       600
atagaaaact taaaaaaca ggaaaccaaa gttgaagatt taaaaatatt aggtgaaacc       660
ataatgggtg tagaaaagaa accgcttcct cacatgcttg ctacaactaa cctgatactt       720
catgatattg atgtgccaaa cataaaacat gataattctt tgatgaagaa tgtaagagat       780
ttaaagcctt cagaatatgt ggatgtaata gcaatgaatc ctcctttgg cggaattgaa        840
```

```
gaagatatgg tactaactaa tttccctcag cagtttcaaa caaagaaac agcagattta    900 tttatgactc ttataatgta tagattaagt gaaaaaggaa gagcgggagt agtacttcca    960
gatggatttt tatttggtga aggtgtaaag actcatataa aagaaaaact tttaaatgaa   1020
tttaaccttc atactatagt aagaatgcct aatggagtat tgccccata tacgggaata   1080 aatacaaacc ttttattctt tgaaaaaggt aagccaacag aagaagtttg gttctttgaa   1140
catccacttc ctgaaggata taaaaattat actaaaacca accaataag atatgaagaa   1200 tttgaactgg agaagaagtg gtggaataac agagaagaaa atgagtatgc gtggaaggtt   1260
tcagtagagg acattaaaaa tagaaattat aatttagatt ataaaaatcc taataaggaa   1320
gaagaagatt taggagatcc aaaggcatta ttaaaaaaat atcatgaagc tgctgctgat   1380
gtagataaat tgcaagattc tttgatagat gaattaaaga agattttaga agggacatca   1440
aaatag                                                              1446

<210> SEQ ID NO 4
<211> LENGTH: 481
<212> TYPE: PRT
<213> ORGANISM: Artificial Sequence
<220> FEATURE:
<223> OTHER INFORMATION: Amino acid sequence of Mtase I-2

<400> SEQUENCE: 4

Met Ser Ile Thr Asn Val Val Lys Ser Val Gln Asp Ile Met Arg Gln
 1               5                   10                  15

Asp Ala Gly Val Asp Gly Asp Ala Gln Arg Ile Ser Gln Leu Val Trp
                20                  25                  30

Met Ile Phe Leu Lys Val Phe Asp Ala Lys Glu Glu Glu Trp Glu Leu
            35                  40                  45

Glu Tyr Asp Asp Tyr Thr Pro Ile Ile Pro Glu Glu Leu Arg Trp Ser
        50                  55                  60

Asn Trp Ala Gln Asp Asp Glu Gly Ile Thr Gly Asp Glu Leu Leu Asp
 65                 70                  75                  80

Phe Val Asn Asn Lys Leu Phe Lys Gly Leu Lys Glu Met Glu Val Asp
                85                  90                  95

Glu Asn Ser Asp Ala Lys Ala Leu Leu Val Lys Ser Val Phe Glu Asp
               100                 105                 110

Ser Tyr Asn Tyr Met Lys Ser Gly Ala Leu Met Arg Gln Val Ile Asn
           115                 120                 125

Lys Leu Asn Glu Ile Asp Phe Thr Ala Gly Glu Asp Arg His Leu Phe
       130                  135                140

Asn Asp Ile Tyr Glu Asn Ile Leu Lys Asp Leu Gln Ser Ala Gly Asn
145                 150                 155                 160

Ala Gly Glu Phe Tyr Thr Pro Arg Pro Val Thr Gln Phe Ile Ile Asp
                165                 170                 175

Met Leu Ser Pro Lys Leu Gly Glu Lys Val Ala Asp Phe Ala Cys Gly
            180                 185                 190

Thr Gly Gly Phe Leu Thr Cys Ala Ile Glu Asn Leu Lys Lys Gln Glu
        195                 200                 205

Thr Lys Val Glu Asp Leu Lys Ile Leu Gly Glu Thr Ile Met Gly Val
    210                 215                 220

Glu Lys Lys Pro Leu Pro His Met Leu Ala Thr Thr Asn Leu Ile Leu
225                 230                 235                 240

His Asp Ile Asp Val Pro Asn Ile Lys His Asp Asn Ser Leu Met Lys
                245                 250                 255
```

```
Asn Val Arg Asp Leu Lys Pro Ser Glu Tyr Val Asp Val Ile Ala Met
            260                 265                 270

Asn Pro Pro Phe Gly Gly Ile Glu Glu Asp Met Val Leu Thr Asn Phe
        275                 280                 285

Pro Gln Gln Phe Gln Thr Lys Glu Thr Ala Asp Leu Phe Met Thr Leu
    290                 295                 300

Ile Met Tyr Arg Leu Ser Glu Lys Gly Arg Ala Gly Val Val Leu Pro
305                 310                 315                 320

Asp Gly Phe Leu Phe Gly Gly Val Lys Thr His Ile Lys Glu Lys
                325                 330                 335

Leu Leu Asn Glu Phe Asn Leu His Thr Ile Val Arg Met Pro Asn Gly
            340                 345                 350

Val Phe Ala Pro Tyr Thr Gly Ile Asn Thr Asn Leu Leu Phe Phe Glu
        355                 360                 365

Lys Gly Lys Pro Thr Glu Glu Val Trp Phe Phe Glu His Pro Leu Pro
    370                 375                 380

Glu Gly Tyr Lys Asn Tyr Thr Leu Thr Lys Pro Ile Arg Tyr Glu Glu
385                 390                 395                 400

Phe Glu Leu Glu Lys Lys Trp Trp Asn Asn Arg Glu Glu Asn Glu Tyr
                405                 410                 415

Ala Trp Lys Val Ser Val Glu Asp Ile Lys Asn Arg Asn Tyr Asn Leu
            420                 425                 430

Asp Tyr Lys Asn Pro Asn Lys Glu Glu Asp Leu Gly Asp Pro Lys
        435                 440                 445

Ala Leu Leu Lys Lys Tyr His Glu Ala Ala Ala Asp Val Asp Lys Leu
    450                 455                 460

Gln Asp Ser Leu Ile Asp Glu Leu Lys Lys Ile Leu Glu Gly Thr Ser
465                 470                 475                 480

Lys

<210> SEQ ID NO 5
<211> LENGTH: 1715
<212> TYPE: DNA
<213> ORGANISM: Artificial Sequence
<220> FEATURE:
<223> OTHER INFORMATION: Polynucleotide sequence of Pptaack and Mtase
      I-1

<400> SEQUENCE: 5
tgattgatta tttattttaa aatgcctaag tgaaatatat acatattata acaataaaat     60
aagtattagt gtaggatttt taaatagagt atctattttc agattaaatt tttgattatt    120
tgatttacat tatataatat tgagtaaagt attgactagc aaaattttt gatactttaa     180 tttgtgaaat ttcttatcaa aagttatatt tttgaataat tttattgaa aaatacaact     240 aaaaaggatt atagtataag tgtgtgtaat tttgtgttaa atttaagggg aggaaaatga    300
atacacagga aatagtaagc aaactttgga acctttgtaa cgtactaaga gatgatggaa    360
taacttatca tcaatatgta acagaattaa catatattct tttcttaaag atggcaaagg    420
aaacaggtac agaggataaa ttgccagaag gttatagatg ggatgattta aaagtttata    480
gaggaatgga acttaagaaa ttttataata aattattaaa ttatcttgga gaaaagacta    540
ctgggatagt gcaaaaaata tatcaggat ctgcaacaaa tatagaagaa ccaaaaaatc    600
tagaaaaaat aattaaaact atagatggat tagattggta ttcagcaaaa gaagaaggac    660
ttggaaactt atatgaagga ttacttgaaa aaaatgcatc tgagaaaaaa tctggtgcag    720
```

```
gacaatactt tactccaaga gtattaatta atgttatggt ggaacttatt gatccaaaac    780
caggtgaaaa atgcaatgac cctgcagcag gaacctttgg atttatgatt gctgcagatc    840
gttacatgaa acagaaaaca gacaactatt ttgatttagg tacagaactt caagagtttc    900
agagaactaa ggcttttcct ggctgtgaat tagttcacga acacatgaga ttagccctta    960
tgaatgctat gcttcatgat atagaaggaa acataatcct cggagatact ttaacaaata   1020
caggaaagca gatgaaagac ttaaatgttg tgctttcaaa ccctccattt ggaactaaaa   1080
gaggtggtga aagagcaaca agagatgatt tgacttacat gacttcaaat aaacaattaa   1140
acttcttgca gcacatatat agaagtttaa aagcagatgg aaaagcaaga gcagctgtgg   1200
tattgccaga taatgtacta tttgatcata atgatggagc gaagattcgt gcggatttaa   1260
tggataaatg taatctacat acaatattac ggttacctac tggtattttc tatgctaaag   1320
gagttaaaac aaatgtgctt ttctttacta gaggtactag tgataaagac aatactaaag   1380
aagtttggat atatgatttg cgtaccaata tgcctagctt tggaaagaca aatcctttaa   1440
agaaagagca ttttgaagac tttataaagg cttatacttc tgaggataga acaaaggtga   1500
aagatgaacg tttttcggta tttactagag aagaaataaa agagaaaaat gataaccttg   1560
acctaggttt aattcgtgat gaaagtgtat tagactatga agatctacaa gatccaattg   1620
aaagtggtga agaaataact tcacaacttg aagaggcaat ggatttaatc caaactgttg   1680
taaagaaact aaagattta ggcggtgaca ggtaa                              1715

<210> SEQ ID NO 6
<211> LENGTH: 1747
<212> TYPE: DNA
<213> ORGANISM: Artificial Sequence
<220> FEATURE:
<223> OTHER INFORMATION: Polynucleotide sequence of Pptaack and MtaseI-2

<400> SEQUENCE: 6
gatcctgatt gattatttat tttaaaatgc ctaagtgaaa tatatacata ttataacaat     60
aaaataagta ttagtgtagg attttttaaat agagtatcta ttttcagatt aaattttga   120 ttattttgatt tacattatat aatattgagt aaagtattga ctagcaaaat tttttgatac   180
tttaatttgt gaaatttctt atcaaaagtt atattttga ataattttta ttgaaaaata    240
caactaaaaa ggattatagt ataagtgtgt gtaattttgt gttaaattta aagggaggaa   300
aatgtcaata acaaacgtag taaaatcagt acaagatata atgcgccagg atgcaggggt   360
agatggagat gctcaaagaa tatctcaact agtttggatg atattttaa aggtatttga    420 tgcaaaagaa gaggaatggg aattagagta tgatgattat acacctatta ttccagaaga   480
attgagatgg agcaactggg ctcaagatga tgaaggaatt acaggcgatg agctttaga    540 ctttgtaaac aataaattat tcaaaggttt aaaggaaatg gaagtagatg agaatagtga   600
tgctaaagct ttattagtta aatctgtatt tgaagattcc tataattata tgaaatcagg   660
agctttaatg aggcaggtaa taataagtt aaatgaaata gattttacag caggtgaaga   720
cagacattta tttaatgata tatatgaaaa tatattaaaa gatcttcaaa gtgcaggcaa   780
tgcaggagaa ttctatacac caagacctgt tacacaattt ataatagata tgctaagtcc   840
aaagcttggt gaaaaagtag ctgactttgc ttgtggtacc ggtggatttt taacatgtgc   900
catagaaaac ttaaaaaaac aggaaaccaa agttgaagat ttaaaaatat taggtgaaac   960
cataatgggt gtagaaaaga aaccgcttcc tcacatgctt gctacaacta acctgatact   1020
tcatgatatt gatgtgccaa acataaaaca tgataattct ttgatgaaga atgtaagaga   1080
```

-continued

| | |
|---|---|
| tttaaagcct tcagaatatg tggatgtaat agcaatgaat cctccttttg gcggaattga | 1140 |
| agaagatatg gtactaacta atttccctca gcagtttcaa acaaaagaaa cagcagattt | 1200 |
| atttatgact cttataatgt atagattaag tgaaaaagga agagcgggag tagtacttcc | 1260 |
| agatggattt ttatttggtg aaggtgtaaa gactcatata aaagaaaaac ttttaaatga | 1320 |
| atttaacctt catactatag taagaatgcc taatggagta tttgccccat atacgggaat | 1380 |
| aaatacaaac cttttattct ttgaaaaagg taagccaaca gaagaagttt ggttctttga | 1440 |
| acatccactt cctgaaggat ataaaaatta tactaaaacc aaaccaataa gatatgaaga | 1500 |
| atttgaactg gagaagaagt ggtggaataa cagagaagaa aatgagtatg cgtggaaggt | 1560 |
| ttcagtagag gacattaaaa atagaaatta aatttagat tataaaaatc ctaataagga | 1620 |
| agaagaagat ttaggagatc caaaggcatt attaaaaaaa tatcatgaag ctgctgctga | 1680 |
| tgtagataaa ttgcaagatt ctttgataga tgaattaaag aagatttag aagggacatc | 1740 |
| aaaatag | 1747 |

<210> SEQ ID NO 7
<211> LENGTH: 3160
<212> TYPE: DNA
<213> ORGANISM: Artificial Sequence
<220> FEATURE:
<223> OTHER INFORMATION: Polynucleotide sequence of Pptaack-MTI-12

<400> SEQUENCE: 7

| | |
|---|---|
| tgattgatta tttatttaa aatgcctaag tgaaatatat acatattata acaataaaat | 60 |
| aagtattagt gtaggatttt taaatagagt atctatttc agattaaatt tttgattatt | 120 |
| tgatttacat tatataatat tgagtaaagt attgactagc aaaatttttt gatactttaa | 180 |
| tttgtgaaat ttcttatcaa aagttatatt tttgaataat ttttattgaa aaatacaact | 240 |
| aaaaaggatt atagtataag tgtgtgtaat tttgtgttaa atttaaaggg aggaaaatga | 300 |
| atacacagga aatagtaagc aaactttgga acctttgtaa cgtactaaga gatgatggaa | 360 |
| taacttatca tcaatatgta acagaattaa catatattct tttcttaaag atggcaaagg | 420 |
| aaacaggtac agaggataaa ttgccagaag gttatagatg ggatgattta aaagtttata | 480 |
| gaggaatgga acttaagaaa ttttataata aattattaaa ttatcttgga gaaaagacta | 540 |
| ctgggatagt gcaaaaaata tatcagggat ctgcaacaaa tatagaagaa ccaaaaaatc | 600 |
| tagaaaaaat aattaaaact atagatggat tagattggta ttcagcaaaa gaagaaggac | 660 |
| ttggaaactt atatgaagga ttacttgaaa aaaatgcatc tgagaaaaaa tctggtgcag | 720 |
| gacaatactt tactccaaga gtattaatta atgttatggt ggaacttatt gatccaaaac | 780 |
| caggtgaaaa atgcaatgac cctgcagcag gaacctttgg atttatgatt gctgcagatc | 840 |
| gttacatgaa acagaaaaca gacaactatt tgatttagg tacagaactt caagagtttc | 900 |
| agagaactaa ggcttttct ggctgtgaat tagttcacga acacatagaa ttagcccctta | 960 |
| tgaatgctat gcttcatgat atagaaggaa acataatcct cggagatact ttaacaaata | 1020 |
| caggaaagca gatgaaagac ttaaatgttg tgctttcaaa ccctccatttt ggaactaaaa | 1080 |
| gaggtggtga aagagcaaca agagatgatt tgacttacat gacttcaaat aaacaattaa | 1140 |
| acttcttgca gcacatatat agaagtttaa aagcagatgg aaaagcaaga gcagctgtgg | 1200 |
| tattgccaga taatgtacta tttgatcata atgatggagc gaagattcgt gcggatttaa | 1260 |
| tggataaatg taatctacat acaatattac ggttacctac tggtattttc tatgctaaag | 1320 |
| gagttaaaac aaatgtgctt ttctttacta gaggtactag tgataaagac aatactaaag | 1380 |

```
aagtttggat atatgatttg cgtaccaata tgcctagctt tggaaagaca atcctttaa    1440 agaaagagca ttttgaagac tttataaagg cttatacttc tgaggataga acaaggtga    1500 aagatgaacg tttttcggta tttactagag aagaaataaa agagaaaaat gataaccttg    1560
acctaggttt aattcgtgat gaaagtgtat tagactatga agatctacaa gatccaattg    1620
aaagtggtga agaaataact tcacaacttg aagaggcaat ggatttaatc caaactgttg    1680
taaagaaact aaagattttta ggcggtgaca ggtaatgtca ataacaaacg tagtaaaatc    1740
agtacaagat ataatgcgcc aggatgcagg ggtagatgga gatgctcaaa gaatatctca    1800
actagtttgg atgatatttt taaaggtatt tgatgcaaaa aagaggaat gggaattaga    1860 gtatgatgat tatacaccta ttattccaga agaattgaga tggagcaact gggctcaaga    1920
tgatgaagga attacaggcg atgagctttt agactttgta aacaataaat tattcaaagg    1980
tttaaaggaa atggaagtag atgagaatag tgatgctaaa gctttattag ttaaatctgt    2040
atttgaagat tcctataatt atatgaaatc aggagcttta atgaggcagg taataaataa    2100
gttaaatgaa atagatttta cagcaggtga agacagacat ttatttaatg atatatatga    2160
aaatatatta aaagatcttc aaagtgcagg caatgcagga gaattctata caccaagacc    2220
tgttacacaa tttataatag atatgctaag tccaaagctt ggtgaaaaag tagctgactt    2280
tgcttgtggt accggtggat ttttaacatg tgccatagaa aacttaaaaa aacaggaaac    2340
caaagttgaa gatttaaaaa tattaggtga accataatg ggtgtagaaa agaaccgct    2400 tcctcacatg cttgctacaa ctaacctgat acttcatgat attgatgtgc caaacataaa    2460
acatgataat tctttgatga agaatgtaag agatttaaag ccttcagaat atgtggatgt    2520
aatagcaatg aatcctcctt ttggcggaat tgaagaagat atggtactaa ctaatttccc    2580
tcagcagttt caaacaaaag aaacagcaga tttatttatg actcttataa tgtatagatt    2640
aagtgaaaaa ggaagagcgg gagtagtact tccagatgga ttttttatttg gtgaaggtgt    2700 aaagactcat ataaagaaa aacttttaaa tgaatttaac cttcatacta tagtaagaat    2760
gcctaatgga gtatttgccc catatacggg aataaataca aaccttttat tctttgaaaa    2820
aggtaagcca acagaagaag tttggttctt tgaacatcca cttcctgaag gatataaaaa    2880
ttatactaaa accaaaccaa taagatatga agaatttgaa ctggagaaga agtggtggaa    2940
taacagagaa gaaatgagt atgcgtggaa ggtttcagta gaggacatta aaaatagaaa    3000
ttataattta gattataaaa atcctaataa ggaagaagaa gatttaggag atccaaaggc    3060
attattaaaa aaatatcatg aagctgctgc tgatgtagat aaattgcaag attctttgat    3120
agatgaatta aagaagattt tagaagggac atcaaaatag                          3160
```

<210> SEQ ID NO 8
<211> LENGTH: 953
<212> TYPE: PRT
<213> ORGANISM: Artificial Sequence
<220> FEATURE:
<223> OTHER INFORMATION: Amino acid sequences of MTI-12

<400> SEQUENCE: 8

```
Met Asn Thr Gln Glu Ile Val Ser Lys Leu Trp Asn Leu Cys Asn Val
1               5                   10                  15

Leu Arg Asp Asp Gly Ile Thr Tyr His Gln Tyr Val Thr Glu Leu Thr
                20                  25                  30

Tyr Ile Leu Phe Leu Lys Met Ala Lys Glu Thr Gly Thr Glu Asp Lys
            35                  40                  45
```

```
Leu Pro Glu Gly Tyr Arg Trp Asp Asp Leu Lys Val Tyr Arg Gly Met
 50                  55                  60

Glu Leu Lys Lys Phe Tyr Asn Lys Leu Leu Asn Tyr Leu Gly Glu Lys
 65                  70                  75                  80

Thr Thr Gly Ile Val Gln Lys Ile Tyr Gln Gly Ser Ala Thr Asn Ile
                 85                  90                  95

Glu Glu Pro Lys Asn Leu Glu Lys Ile Ile Lys Thr Ile Asp Gly Leu
            100                 105                 110

Asp Trp Tyr Ser Ala Lys Glu Gly Leu Gly Asn Leu Tyr Glu Gly
        115                 120                 125

Leu Leu Glu Lys Asn Ala Ser Glu Lys Lys Ser Gly Ala Gly Gln Tyr
130                 135                 140

Phe Thr Pro Arg Val Leu Ile Asn Val Met Val Glu Leu Ile Asp Pro
145                 150                 155                 160

Lys Pro Gly Glu Lys Cys Asn Asp Pro Ala Ala Gly Thr Phe Gly Phe
                165                 170                 175

Met Ile Ala Ala Asp Arg Tyr Met Lys Gln Lys Thr Asp Asn Tyr Phe
            180                 185                 190

Asp Leu Gly Thr Glu Leu Gln Glu Phe Gln Arg Thr Lys Ala Phe Ser
        195                 200                 205

Gly Cys Glu Leu Val His Glu Thr His Arg Leu Ala Leu Met Asn Ala
210                 215                 220

Met Leu His Asp Ile Glu Gly Asn Ile Ile Leu Gly Asp Thr Leu Thr
225                 230                 235                 240

Asn Thr Gly Lys Gln Met Lys Asp Leu Asn Val Val Leu Ser Asn Pro
                245                 250                 255

Pro Phe Gly Thr Lys Arg Gly Gly Glu Arg Ala Thr Arg Asp Asp Leu
            260                 265                 270

Thr Tyr Met Thr Ser Asn Lys Gln Leu Asn Phe Leu Gln His Ile Tyr
        275                 280                 285

Arg Ser Leu Lys Ala Asp Gly Lys Ala Arg Ala Ala Val Val Leu Pro
290                 295                 300

Asp Asn Val Leu Phe Asp His Asn Asp Gly Ala Lys Ile Arg Ala Asp
305                 310                 315                 320

Leu Met Asp Lys Cys Asn Leu His Thr Ile Leu Arg Leu Pro Thr Gly
                325                 330                 335

Ile Phe Tyr Ala Lys Gly Val Lys Thr Asn Val Leu Phe Phe Thr Arg
            340                 345                 350

Gly Thr Ser Asp Lys Asp Asn Thr Lys Glu Val Trp Ile Tyr Asp Leu
        355                 360                 365

Arg Thr Asn Met Pro Ser Phe Gly Lys Thr Asn Pro Leu Lys Lys Glu
370                 375                 380

His Phe Glu Asp Phe Ile Lys Ala Tyr Thr Ser Glu Asp Arg Thr Lys
385                 390                 395                 400

Val Lys Asp Glu Arg Phe Ser Val Phe Thr Arg Glu Glu Ile Lys Glu
                405                 410                 415

Lys Asn Asp Asn Leu Asp Leu Gly Leu Ile Arg Asp Glu Ser Val Leu
            420                 425                 430

Asp Tyr Glu Asp Leu Gln Asp Pro Ile Glu Ser Gly Glu Glu Ile Thr
        435                 440                 445

Ser Gln Leu Glu Glu Ala Met Asp Leu Ile Gln Thr Val Val Lys Lys
450                 455                 460
```

-continued

```
Leu Lys Ile Leu Gly Gly Asp Arg Met Ser Ile Thr Asn Val Val Lys
465                 470                 475                 480

Ser Val Gln Asp Ile Met Arg Gln Asp Ala Gly Val Asp Gly Asp Ala
            485                 490                 495

Gln Arg Ile Ser Gln Leu Val Trp Met Ile Phe Leu Lys Val Phe Asp
            500                 505                 510

Ala Lys Glu Glu Glu Trp Glu Leu Glu Tyr Asp Asp Tyr Thr Pro Ile
            515                 520                 525

Ile Pro Glu Glu Leu Arg Trp Ser Asn Trp Ala Gln Asp Asp Glu Gly
            530                 535                 540

Ile Thr Gly Asp Glu Leu Leu Asp Phe Val Asn Asn Lys Leu Phe Lys
545                 550                 555                 560

Gly Leu Lys Glu Met Glu Val Asp Glu Asn Ser Asp Ala Lys Ala Leu
            565                 570                 575

Leu Val Lys Ser Val Phe Glu Asp Ser Tyr Asn Tyr Met Lys Ser Gly
            580                 585                 590

Ala Leu Met Arg Gln Val Ile Asn Lys Leu Asn Glu Ile Asp Phe Thr
            595                 600                 605

Ala Gly Glu Asp Arg His Leu Phe Asn Asp Ile Tyr Glu Asn Ile Leu
            610                 615                 620

Lys Asp Leu Gln Ser Ala Gly Asn Ala Gly Glu Phe Tyr Thr Pro Arg
625                 630                 635                 640

Pro Val Thr Gln Phe Ile Ile Asp Met Leu Ser Pro Lys Leu Gly Glu
            645                 650                 655

Lys Val Ala Asp Phe Ala Cys Gly Thr Gly Gly Phe Leu Thr Cys Ala
            660                 665                 670

Ile Glu Asn Leu Lys Lys Gln Glu Thr Lys Val Glu Asp Leu Lys Ile
            675                 680                 685

Leu Gly Glu Thr Ile Met Gly Val Glu Lys Lys Pro Leu Pro His Met
            690                 695                 700

Leu Ala Thr Thr Asn Leu Ile Leu His Asp Ile Asp Val Pro Asn Ile
705                 710                 715                 720

Lys His Asp Asn Ser Leu Met Lys Asn Val Arg Asp Leu Lys Pro Ser
            725                 730                 735

Glu Tyr Val Asp Val Ile Ala Met Asn Pro Pro Phe Gly Gly Ile Glu
            740                 745                 750

Glu Asp Met Val Leu Thr Asn Phe Pro Gln Gln Phe Gln Thr Lys Glu
            755                 760                 765

Thr Ala Asp Leu Phe Met Thr Leu Ile Met Tyr Arg Leu Ser Glu Lys
770                 775                 780

Gly Arg Ala Gly Val Val Leu Pro Asp Gly Phe Leu Phe Gly Glu Gly
785                 790                 795                 800

Val Lys Thr His Ile Lys Glu Lys Leu Leu Asn Glu Phe Asn Leu His
            805                 810                 815

Thr Ile Val Arg Met Pro Asn Gly Val Phe Ala Pro Tyr Thr Gly Ile
            820                 825                 830

Asn Thr Asn Leu Leu Phe Phe Glu Lys Gly Lys Pro Thr Glu Glu Val
            835                 840                 845

Trp Phe Phe Glu His Pro Leu Pro Glu Gly Tyr Lys Asn Tyr Thr Lys
            850                 855                 860

Thr Lys Pro Ile Arg Tyr Glu Glu Phe Glu Leu Glu Lys Lys Trp Trp
865                 870                 875                 880
```

| | | | |
|---|---|---|---|
| Asn Asn Arg Glu | Glu Asn Glu Tyr | Ala Trp Lys Val | Ser Val Glu Asp |
| 885 | | 890 | 895 |

Ile Lys Asn Arg Asn Tyr Asn Leu Asp Tyr Lys Asn Pro Asn Lys Glu
    900                          905                       910

Glu Glu Asp Leu Gly Asp Pro Lys Ala Leu Leu Lys Lys Tyr His Glu
       915                     920                    925

Ala Ala Ala Asp Val Asp Lys Leu Gln Asp Ser Leu Ile Asp Glu Leu
 930               935                    940

Lys Lys Ile Leu Glu Gly Thr Ser Lys
945               950

<210> SEQ ID NO 9
<211> LENGTH: 1670
<212> TYPE: DNA
<213> ORGANISM: Artificial Sequence
<220> FEATURE:
<223> OTHER INFORMATION: Polynucleotide sequence of MTII-1

<400> SEQUENCE: 9

| | | | | |
|---|---|---|---|---|
| atgcataagt | ggcgtgattt | atctatactt | ggagaaatgt | atgaaagatc aatggaaaag | 60 |
| gaagaaagaa | aacggaaggg | gagttttat | actcctcatt | acatagttga ctatatagtg | 120 |
| aagaatatta | tgtcaaattt | agatcttaaa | aaaatcctt | ttataaaagt attagatcct | 180 |
| tcttgtggaa | gtggatattt | tctagtaaga | gtatacgaaa | ttttaatgga aaagttcagt | 240 |
| caaaatttag | agcacattag | aaatactttt | aacgataaaa | cttataccat tgaaactgaa | 300 |
| gatggattaa | agagtataga | cggatttcac | tattggcagc | aggaaaattt aagctttcat | 360 |
| atattaaaga | aatgtatata | tggtgcagat | atagacagca | tcgctgtaga gcttacaaaa | 420 |
| attaatttaa | gtaaagtcag | tggtataaac | attaatatgg | aggacaatat catatgctgc | 480 |
| aacagtctta | taaagtggaa | tcaaattgat | aatgtagaaa | aatataagga atctaatatt | 540 |
| caatctgttg | ttaagttttg | gaacacaaaa | tatgattatg | tactggggaa tcctccttgg | 600 |
| gtatctttaa | gtcgaaagaa | taagatgaat | atagaggatg | gattgttaaa gtattatagt | 660 |
| gaaaattata | tggaaatac | atattacct | aatttgtatg | agtattttat aaaaaggtct | 720 |
| atggaaatat | taaagccggg | aggaagattt | ggatttgtag | ttcctgatag gctgtcacga | 780 |
| aatcttcaat | acagtgaact | tagaaagagt | ttacttgaaa | attataatat attaaatctt | 840 |
| gtgtttgaga | tagattttcc | ggaaataaac | acagattcta | tgattatgat agcagaaaat | 900 |
| aaacatagaa | aagtaaataa | aatagaaata | gatatttata | agaagaggac atatgaaatg | 960 |
| tatcagcatg | aatatctgag | aaattcaaaa | tttaagttta | catattgttg ttataatcaa | 1020 |
| aacttaagca | taaaggattg | tatagagaaa | aatagcagca | aattaaaaag catttccaag | 1080 |
| acttttacag | gatttatagg | ttatagtaaa | aaataactc | ctgttaaaaa aaatcaacat | 1140 |
| caggttgaag | tattaaaagg | ggaaaatata | aaaaagtttc | gagttttaaa caattactat | 1200 |
| tatgattttg | tgcctgaaaa | cataataggc | ggaactaaaa | atatagaaaa acttactttt | 1260 |
| aaaaataaat | tagtaataag | gaaaactgga | aaaaatttaa | tagcagcttt agatgataag | 1320 |
| ggacgtataa | tagaacaatc | tctatatgga | ataataagta | caaatgagga attttcacct | 1380 |
| cagtatattt | tggcaatatt | gaattcagag | ttaattcaat | ggtattattt aaattttta | 1440 |
| attaccaact | ctaattctat | tccacaaatt | aaaaaatgca | atttggatga ataccaata | 1500 |
| agacattgca | gcagacaagc | taagaagac | atagaaaaat | tagtttgcaa aattataaat | 1560 |

```
gataatgatc aaaaaaatat gttgaagaaa atattagatg atgagatatt tgaattatat    1620
aatattgatc ataattatag aagaattata ttaaatgata ttgaaaataa                1670
```

<210> SEQ ID NO 10
<211> LENGTH: 556
<212> TYPE: PRT
<213> ORGANISM: Artificial Sequence
<220> FEATURE:
<223> OTHER INFORMATION: Amino acid sequence of MTII-1

<400> SEQUENCE: 10

```
Met His Lys Trp Arg Asp Leu Ser Ile Leu Gly Glu Met Tyr Glu Arg
1               5                   10                  15

Ser Met Glu Lys Glu Arg Lys Arg Lys Gly Ser Phe Tyr Thr Pro
            20                  25                  30

His Tyr Ile Val Asp Tyr Ile Val Lys Asn Ile Met Ser Asn Leu Asp
            35                  40                  45

Leu Lys Lys Asn Pro Phe Ile Lys Val Leu Asp Pro Ser Cys Gly Ser
        50                  55                  60

Gly Tyr Phe Leu Val Arg Val Tyr Glu Ile Leu Met Glu Lys Phe Ser
65                  70                  75                  80

Gln Asn Leu Glu His Ile Arg Asn Thr Phe Asn Asp Lys Thr Tyr Thr
                85                  90                  95

Ile Glu Thr Glu Asp Gly Leu Lys Ser Ile Asp Gly Phe His Tyr Trp
            100                 105                 110

Gln Gln Glu Asn Leu Ser Phe His Ile Leu Lys Lys Cys Ile Tyr Gly
        115                 120                 125

Ala Asp Ile Asp Ser Ile Ala Val Glu Leu Thr Lys Ile Asn Leu Ser
    130                 135                 140

Lys Val Ser Gly Ile Asn Ile Asn Met Glu Asp Asn Ile Ile Cys Cys
145                 150                 155                 160

Asn Ser Leu Ile Lys Trp Asn Gln Ile Asp Asn Val Glu Lys Tyr Lys
                165                 170                 175

Glu Ser Asn Ile Gln Ser Val Val Lys Phe Trp Asn Thr Lys Tyr Asp
            180                 185                 190

Tyr Val Leu Gly Asn Pro Pro Trp Val Ser Leu Ser Arg Lys Asn Lys
        195                 200                 205

Met Asn Ile Glu Asp Gly Leu Leu Lys Tyr Tyr Ser Glu Asn Tyr Asn
    210                 215                 220

Gly Asn Thr Tyr Leu Pro Asn Leu Tyr Glu Tyr Phe Ile Lys Arg Ser
225                 230                 235                 240

Met Glu Ile Leu Lys Pro Gly Gly Arg Phe Gly Phe Val Val Pro Asp
                245                 250                 255

Arg Leu Ser Arg Asn Leu Gln Tyr Ser Glu Leu Arg Lys Ser Leu Leu
            260                 265                 270

Glu Asn Tyr Asn Ile Leu Asn Leu Val Phe Glu Ile Asp Phe Pro Glu
        275                 280                 285

Ile Asn Thr Asp Ser Met Ile Met Ile Ala Glu Asn Lys His Arg Lys
    290                 295                 300

Val Asn Lys Ile Glu Ile Asp Ile Tyr Lys Lys Arg Thr Tyr Glu Met
305                 310                 315                 320

Tyr Gln His Glu Tyr Leu Arg Asn Ser Lys Phe Lys Phe Thr Tyr Cys
                325                 330                 335

Cys Tyr Asn Gln Asn Leu Ser Ile Lys Asp Cys Ile Glu Lys Asn Ser
            340                 345                 350
```

```
Ser Lys Leu Lys Ser Ile Ser Lys Thr Phe Thr Gly Phe Ile Gly Tyr
        355                 360                 365

Ser Lys Lys Ile Thr Pro Val Lys Lys Asn Gln His Gln Val Glu Val
    370                 375                 380

Leu Lys Gly Glu Asn Ile Lys Lys Phe Arg Val Leu Asn Asn Tyr Tyr
385                 390                 395                 400

Tyr Asp Phe Val Pro Glu Asn Ile Ile Gly Gly Thr Lys Asn Ile Glu
                405                 410                 415

Lys Leu Thr Phe Lys Asn Lys Leu Val Ile Arg Lys Thr Gly Lys Asn
            420                 425                 430

Leu Ile Ala Ala Leu Asp Asp Lys Gly Arg Ile Ile Glu Gln Ser Leu
        435                 440                 445

Tyr Gly Ile Ile Ser Thr Asn Glu Glu Phe Ser Pro Gln Tyr Ile Leu
    450                 455                 460

Ala Ile Leu Asn Ser Glu Leu Ile Gln Trp Tyr Tyr Leu Asn Phe Leu
465                 470                 475                 480

Ile Thr Asn Ser Asn Ser Ile Pro Gln Ile Lys Lys Cys Asn Leu Asp
                485                 490                 495

Glu Ile Pro Ile Arg His Cys Ser Arg Gln Ala Lys Glu Asp Ile Glu
            500                 505                 510

Lys Leu Val Cys Lys Ile Ile Asn Asp Asn Asp Gln Lys Asn Met Leu
        515                 520                 525

Lys Lys Ile Leu Asp Asp Glu Ile Phe Glu Leu Tyr Asn Ile Asp His
    530                 535                 540

Asn Tyr Arg Arg Ile Ile Leu Asn Asp Ile Glu Asn
545                 550                 555
```

<210> SEQ ID NO 11
<211> LENGTH: 1944
<212> TYPE: DNA
<213> ORGANISM: Artificial Sequence
<220> FEATURE:
<223> OTHER INFORMATION: Polynucleotide sequence of Ppta-ack-MTII-1

<400> SEQUENCE: 11

```
tgcctaagtg aaatatatac atattataac aataaaataa gtattagtgt aggattttta     60
aatagagtat ctattttcag attaaatttt tgattatttg atttacatta tataatattg    120
agtaaagtat tgactagcaa aattttttga tactttaatt tgtgaaattt cttatcaaaa    180
gttatatttt tgaataattt ttattgaaaa atacaactaa aaaggattat agtataagtg    240
tgtgtaattt tgtgttaaat ttaaagggag gaaaatgcat aagtggcgtg atttatctat    300
acttggagaa atgtatgaaa gatcaatgga aaaggaagaa agaaaacgga aggggagttt    360
ttatactcct cattacatag ttgactatat agtgaagaat attatgtcaa atttagatct    420
taaaaaaaat ccttttataa aagtattaga tccttcttgt ggaagtggat attttctagt    480
aagagtatac gaaattttaa tggaaaagtt cagtcaaaat ttagagcaca ttagaaatac    540
ttttaacgat aaaacttata ccattgaaac tgaagatgga ttaaagagta tagacggatt    600
tcactattgg cagcaggaaa atttaagctt tcatatatta aagaaatgta tatatggtgc    660
agatatagac agcatcgctg tagagcttac aaaaattaat ttaagtaaag tcagtggtat    720
aaacattaat atggaggaca atatcatatg ctgcaacagt cttataaagt ggaatcaaat    780
tgataatgta gaaaaatata aggaatctaa tattcaatct gttgttaagt tttggaacac    840
aaaatatgat tatgtactgg ggaatcctcc ttgggtatct ttaagtcgaa agaataagat    900
```

```
gaatatagag gatggattgt taaagtatta tagtgaaaat tataatggaa atacatattt    960
acctaatttg tatgagtatt ttataaaaag gtctatggaa atattaaagc cgggaggaag   1020
atttggattt gtagttcctg ataggctgtc acgaaatctt caatacagtg aacttagaaa   1080
gagtttactt gaaaattata atatattaaa tcttgtgttt gagatagatt ttccggaaat   1140
aaacacagat tctatgatta tgatagcaga aaataaacat agaaaagtaa ataaaataga   1200
aatagatatt tataagaaga ggacatatga aatgtatcag catgaatatc tgagaaattc   1260
aaaatttaag tttacatatt gttgttataa tcaaaactta agcataaagg attgtataga   1320
gaaaaatagc agcaaattaa aaagcatttc caagactttt acaggattta taggttatag   1380
taaaaaaata actcctgtta aaaaaaatca acatcaggtt gaagtattaa aaggggaaaa   1440
tataaaaaag tttcgagttt taaacaatta ctattatgat tttgtgcctg aaaacataat   1500
aggcggaact aaaaatatag aaaaacttac ttttaaaaat aaattagtaa taaggaaaac   1560
tggaaaaaat ttaatagcag ctttagatga taagggacgt ataatagaac aatctctata   1620
tggaataata agtacaaatg aggaattttc acctcagtat attttggcaa tattgaattc   1680
agagttaatt caatggtatt atttaaattt tttaattacc aactctaatt ctattccaca   1740
aattaaaaaa tgcaatttgg atgaaatacc aataagacat tgcagcagac aagctaaaga   1800
agacatagaa aaattagttt gcaaaattat aaatgataat gatcaaaaaa atatgttgaa   1860
gaaaatatta gatgatgaga tatttgaatt atataatatt gatcataatt atagaagaat   1920
tatattaaat gatattgaaa ataa                                          1944
```

USE OF CLOSTRIDIAL METHYLTRANSFERASES FOR GENERATING NOVEL STRAINS

This application is a continuation of U.S. application Ser. No. 14/209,634 filed Mar. 13, 2014, which claims the benefit of priority to U.S. Provisional Application 61/780,731 filed Mar. 13, 2013 the disclosure of which are hereby incorporated by reference in their entirety.

FIELD OF THE INVENTION

The present invention relates to isolated polynucleotides encoding DNA Type I methyltransferase and uses thereof for improving transformation efficiencies of exogenous and endogenous plasmid DNA into *Clostridia*.

BACKGROUND OF THE INVENTION

Genetic manipulation of many bacterial genera can often be difficult due to host restriction systems. These systems are designed to prevent foreign DNA from stably expressing and maintaining genes (e.g., bacteriophage) that may be disadvantageous to the host. As a result, very few, if any, transformants are obtained except in those rare cases where the process methods have been highly optimized. Even highly optimized methods can produce few transformants and often the results are irreproducible due to variations in physiological parameters of the host cells.

The genus *Clostridia* which include species of medical and industrial importance have historically been difficult to manipulate genetically. Those that have been genetically transformed are few and the efficiencies have been low, typically limited to at most $1\times10^3$ transformants/µg DNA in the most efficient systems (Mermelstein et al., 1993, *Applied and Environmental Microbiology*, 59:1077-1081; Allen and Blaschek, 1990, *FEMS Microbiology Letters*, 58:217) but more often only yield a few recombinant colony forming units (CFU). Integrative plasmids have been used with even less efficiency, typically attaining transformation frequencies no higher than 1 CFU/µg DNA. The prevailing view is that the low transformation frequencies are due to the introduced DNA being degraded during the transformation process by one or more host restriction systems. In those cases where suitable transformation efficiencies in *Clostridium* have been observed and shown to be reproducible, it was often due to blocking of a specific endonuclease site encoding a restriction enzyme (e.g., CacI, *C. acetobutylicum*).

Thus, there remains a need in the art to improve the efficiency of introducing DNA into *Clostridia*.

SUMMARY OF THE INVENTION

The present invention relates to using Clostridial Type I methyltransferases to improve the efficiency of introducing DNA into solventogenic *Clostridia*.

In accordance with the invention, isolated polynucleotides encoding a DNA Type I methyltransferase selected from the group consisting of: a polynucleotide comprising a nucleotide sequence having at least 98% sequence identity with SEQ ID NO: 1; and (b) a polynucleotide encoding a polypeptide having an amino acid sequence at least 85% sequence identity with the polypeptide SEQ ID NO: 2 are provided.

In another aspect, the invention provides an isolated polynucleotide encoding a DNA Type I methyltransferase selected from the group consisting of: (a) a polynucleotide comprising a nucleotide sequence having at least 85% sequence identity with SEQ ID NO: 3; and (b) a polynucleotide encoding a polypeptide having an amino acid sequence at least 87% sequence identity with the polypeptide of SEQ ID NO: 4.

In another aspect, the invention provides an isolated polynucleotide expressed from an operably-linked promoter, phosphotransacetylase-acetate kinase operon (Ppta-ack) and a polynucleotide encoding a polypeptide having an amino acid sequences at least 60% sequence identity with the polypeptide of SEQ ID NO: 7.

In particular embodiments of the invention the polynucleotide is encoded on a methylation vector such as pCOSMTI-1, pCOSMTI-2 or pCOSMTI-12. In other particular embodiments the isolated polynucleotide is expressed from an operably-linked promoter such as Ppta-ack. In particular embodiments the methyltransferase of SEQ ID NO: 1 is expressed with a polynucleotide consisting of the nucleotides 1-296 of SEQ ID NO: 5. In other embodiments the methyltransferase of SEQ ID NO: 3 is expressed with a polynucleotide consisting of the nucleotides 1-296 of SEQ ID NO: 6. In yet other embodiments the methyltransferase of SEQ NO: 7 is expressed with a polynucleotide consisting of the nucleotides 1-296 of SEQ ID NO: 6.

In another aspect, the invention provides methods of generating a bacterial recombinant cell expressing a DNA Type I methyltransferase having biological activities, comprising: (a) introducing a methylation vector into a bacterial host cell wherein said methylation vector expresses a DNA Type I methyltransferase polynucleotide; and (b) introducing a transforming vector into the bacterial host cell wherein said transforming vector comprises plasmid DNA that is methylated by said methylation vector.

In particular embodiments of the invention the DNA Type I methyltransferase polynucleotide is a polynucleotide comprising a nucleotide sequence having at least 98% sequence identity with SEQ ID NO:1, a polynucleotide encoding a polypeptide having an amino acid sequence at least 85% sequence identity with the polypeptide SEQ ID NO: 2, a polynucleotide comprising a nucleotide sequence having at least 85% sequence identity with SEQ ID NO: 3, or a polynucleotide encoding a polypeptide having an amino acid sequence at least 87% sequence identity with the polypeptide of SEQ ID NO: 4.

In other particular embodiments the DNA Type I methyltransferase polynucleotide is expressed from an operably-linked promoter such as Ppta-ack. In particular embodiments of the invention the DNA Type I methyltransferase is encoded on a methylation vector such as pCOSMTI-1, pCOSMTI-2 or pCOSMTI-12.

In particular embodiments the bacterial host cell is *Escherichia coli* (*E. coli*). In yet other embodiments, the second bacterial recipient cell is *Clostridia*.

In particular embodiments the method further comprises purifying and transferring the methylated plasmid DNA from the bacterial host cell to a second bacterial recipient cell that can degrade the plasmid DNA but which cannot degrade the methylated DNA.

In other particular embodiments, the methylated plasmid DNA is transferred from the bacterial host cell to a second bacterial recipient cell by transformation such as electroporation or conjugation. In particular embodiments the transformants of the methylated DNA of the second bacterial host cell comprising methylated DNA are isolated.

In particular embodiments, the methylation vector is transformed into the bacterial host cell along with a shuttle vector such as pACR-1. In other embodiments, the methylation vector is transformed into the bacterial host cell with a conjugation vector such as pACC-1.

BRIEF DESCRIPTION OF THE DRAWINGS

FIGS. 1A and 1B show the genomic (a) and amino acid (b) sequences of Mtase I-1 Type I methyltransferase (MTI-1) identified in the *C. coskatii* genome sequence (SEQ ID NOs: 1 and 2, respectively).

FIGS. 2A and 2B show the genomic (a) and amino acid (b) sequences of Mtase 1-2 Type I methyltransferase (MTI-2) identified in *C. coskatii* (SEQ ID NOs: 3 and 4, respectively).

FIG. 3 shows the genomic sequence of a methyltransferase operon expressed from the Clostridial Pptaack promoter.

Figure 4:
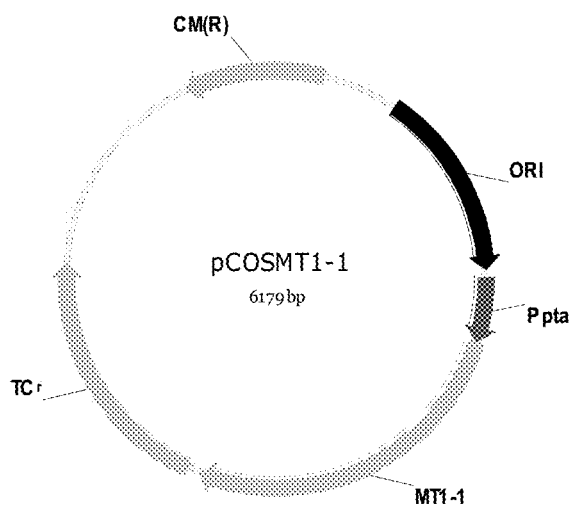
FIG. 4 shows a plasmid map of methylation vector pCOSMTI-1.

FIG. 5 shows a plasmid map of methylation vector pCOSMTI-2.

FIG. 6 shows a plasmid map of doubly methylating vector pCOSMT-12.

FIGS. 7A-7B show plasmid maps of replicating vectors *E. coli-Clostridium* shuttle vectors pACR1 (A) and pACR1Cm (B) containing catP, encoding chloramphenicol resistance.

FIGS. 8A-8B show plasmid maps of conjugation vectors pACC-1 (A) and pACC-1T (B) containing tetR, encoding tetracycline resistance.

FIG. 9 is a Tris-Borate-EDTA gel showing the co-residency of pCOSMTI-1, pACR-1 and pCOSMTI-12, pACC-1 in *E. coli* using restriction analysis. The arrow at left points to a DNA standard of 1500 base pairs.

FIG. 10 shows a plasmid map of a Type II methylating control vector pCOSMTII-1.

DETAILED DESCRIPTION OF THE INVENTION

This invention provides isolated polynucleotides encoding DNA Type I methyltransferase and uses thereof for improving transformation efficiencies of exogenous and endogenous plasmid DNA into Clostridial hosts. This invention further provides plasmid vectors that employ plasmids and sequence compositions that contain homoacetogen Type I methyltransferases expressed from a homoacetogenic Clostridial promoter known to function in *E. coli* and solventogenic *Clostridia*.

Genetic manipulation of bacteria enhances the probability of generating novel strains that can be useful to commercial production processes. The transformation efficiency is significantly reduced by host endonucleases that rapidly degrade foreign DNA introduced by various methods known to those skilled in the art (e.g. electroporation, conjugation, protoplast fusion, etc.). To circumvent host defense mechanisms, one approach to enhance transformation frequency is to modify the DNA before introduction into the recipient cells so that the introduced DNA becomes recalcitrant to degradation.

The restriction modification system (R/M system) is used by bacteria, and perhaps other prokaryotic organisms to protect themselves from foreign DNA, such as the one borne by bacteriophages. Bacteria have restriction enzymes which cleave double stranded DNA at specific points into fragments, which are then degraded further by other endonucleases and exonucleases. Approximately one quarter of known bacteria possess R/M systems and of those about one half have more than one type of system. The following solventogenic *Clostridia* have multiple, diverse R/M systems: *C. coskatii, C. autoethanogenum, C. ragsdalei, C. carboxidivorans, C. ljungdahlii.*

As used herein solventogenic *Clostridia* includes *Clostridia* that have the ability to make solvents such as ethanol either directly in the metabolic pathway or by the reduction of acetate.

Modes of DNA transfer have been shown to induce restriction systems in *Clostridia* so as to prevent routine genetic manipulation of host strains.

Several different types of host restriction systems have been identified and characterized in *Clostridium* (e.g. Types I, II, III, and IV have all been observed in the genomes) and present a variation on a theme in the understanding of the underlying mechanisms of action. The best characterized systems are the Type II restriction systems Feyter et al. 1990, *Journal of Bacteriology,* 173:6421-6427; Mann et al., 1978, *Gene* 3:97-102) and are commercially available. These enzymes recognize a palindromic sequence and upon binding the duplex DNA in the presence of magnesium ions, digest the DNA across both strands at or very near the site of binding. The digestion can generate a blunt end or asymmetrical cleavages with 5' or 3' overhangs.

In contrast, DNA Type I restriction endonucleases bind the DNA at a specific recognition site on the DNA but cut at a significant distance from the recognition site. DNA Type I (EC 3.1.21.3) restriction and modification enzymes are complex multifunctional systems that require ATP, S-adenosylmethionine, and $Mg^{2+}$ as cofactors. They catalyze the endonucleolytic cleavage of DNA to give random, bipartite, interrupted double-stranded fragments with terminal 5'-phosphates. ATP is simultaneously hydrolysed. These systems are widespread in *Clostridium*. The Type I restriction systems contain all the intact genes for a fully functioning restriction-modification system (specificity, methyltransferase and restriction genes) and thus are presumed to be playing an important role in exogenous DNA degradation.

DNA Type I methyltransferase as used herein is a DNA N-6 adenine methyltransferase (E.C. 2.1.1.72). A Type I methyltransferase is an enzyme that recognizes a specific sequence and methylates one of the adenine bases in or near that sequence (Kennaway et al. 2009, *Nucleic Acids Research*, The structure of M.EcoKI Type I DNA methyltransferase with a DNA mimic antirestriction protein, 37(3): 762-770). Foreign DNAs which are not methylated in this manner that are introduced into the host cell are degraded by sequence-specific restriction enzymes. In the present invention, the Type I methylation system comprises the protective component of the restriction-modification system. In particular embodiments of the invention, the Type I methyltransferases are expressed from a known constitutive Clostridial promoter in *E. coli* host strains methylating the DNA at unknown recognition sequences. The DNAs contained in solventogenic *Clostridia* are all AT rich (>70%) and therefore abundant targets exist for the methyltranferase activities encoded by the DNA modification enzymes described herein.

In particular embodiments of the invention, the isolated polynucleotide encoding the DNA Type I methyltransferase is encoded by a nucleotide sequence comprising a nucleotide sequence having at least 98% sequence identity with SEQ ID NO: 1, a polynucleotide encoding a polypeptide having an amino acid sequence at least 85% sequence identity with the polypeptide SEQ ID NO: 2, a polynucleotide comprising a nucleotide sequence having at least 85% sequence identity with SEQ ID NO: 3, or a polynucleotide encoding a polypeptide having an amino acid sequence at least 87% sequence identity with the polypeptide of SEQ ID NO: 4. In other embodiments of the invention, the DNA Type I methyltransferase is encoded by a polynucleotide that hybridizes under high stringency conditions with nucleotides 1-1446 of SEQ ID NO: 3 or its full-length complimentary strand or a polynucleotide that hybridizes under high stringency conditions with nucleotides 1-1446 of SEQ ID NO: 3 or its full-length complimentary strand.

The isolated polynucleotide encoding the DNA Type I methyltransferase can be expressed using a strong constitutive Clostridial promoter such as Pptaack. In particular embodiments, the polynucleotide expressed from an operably linked promoter is a polynucleotide having an amino acid sequences at least 60% sequence identity with the polypeptide of SEQ ID NO: 7 or a polynucleotide that hybridizes under high stringency conditions with nucleotides 1-2864 of SEQ ID NO: 7 or its full-length complimentary strand.

As used herein high stringency conditions refers to conditions under which the polypeptide will hybridize to a target sequence. For example, high stringency conditions include hybridization at 50° C. in 5×SSPE, 0.25% SDS and washed 2 times in hybridization wash buffer composed of 2×SSC, 0.2% SDS at 65° C.

As used herein operably-linked means joined as part of the same nucleic acid molecule, suitably positioned and oriented for transcription to be initiated from the promoter. DNA operably linked to a promoter is under transcriptional initiation regulation of the promoter or in functional combination therewith.

The isolated polynucleotides encoding DNA Type I methyltransferase can be used in methods to generate a bacterial host recombinant cell expressing a DNA Type I methyltransferase having biological activities. The method comprises introducing a methylation vector into the bacterial host cell. As used herein a methylation vector is a plasmid vector containing a cloned Type I methyltransferase polynucleotide from a homoacetogenic *Clostridium*. Suitable methylation vectors include, but are not limited to pCOSMTI-1 (comprising a cloned MTI-1 Type I methyltransferase polynucleotide), pCOSMTI-2 (comprising a cloned MTI-2 Type I methyltransferase polynucleotide) and pCOSMTI-12 (comprising cloned MTI-1 and MTI-2 Type I methyltransferase polynucleotides). The sequences of the cloned Type I methyltransferase can be expressed in *E. coli* and *Clostridia* from an operably-linked Clostridial promoter, such as Pptaack, to ensure adequate methylation in both a heterologous and a recipient cell. The method further comprises introducing a transforming vector into the bacterial host cell wherein said transforming vector comprises plasmid DNA that is methylated by said methylation vector.

Suitable bacterial host cells containing the methylation vectors include but are not limited to gram negative bacteria such as *E. coli* and closely related Enterobacteriaceae including *Salmonella* spp., *Yersinia* spp., *Klebsiella* spp. *Shigella* spp. *Enterobacter* spp., *Serratia* spp. and *Citrobacter* spp.

The methyltransferase polynucleotides can also be expressed from a replicating broad-host range vector based on the pBBR-1 replicon, originally isolated from Bortadella *bronchiseptica* S87 (Antoine. and Locht. (1992) *Mol. Microbiol.* 6(13): 1785-1799). The range of genera known to stably replicate pBBR-1-based plasmids includes representatives from *Aeromonas, Acetobacter, Agrobacterium, Alcaligenes, Azorizobium, Bartonella, Bordetella, Brucella, Caulobacter, Escherichia, Hyphomicrobium, Methylobacillus, Methylbacterium, Methylophilus, Pseudomonas. Paracoccus, Rhizobium, Rhodobacter Salmonella Vibrio* and *Xanthomonas*.

In molecular cloning, a vector is a DNA molecule used as a vehicle to artificially carry native or foreign genetic material into another cell, where it can be replicated and/or expressed. A vector containing foreign DNA is termed recombinant DNA. The four major types of vectors are plasmids, viral vectors, cosmids, and artificial chromosomes. Common to all engineered vectors are an origin of replication, a multicloning site, and a selectable marker.

The methylation vector and the transforming vector can be first transferred into an *E. coli* methylation-minus strain GM2163. Co-residing vectors in this host environment will be methylated only to the extent of Type I methyltransferase expression and sequence recognition. Cloned sequences will contain homoacetogenic Clostridial DNA so methylated sites are expected to be present. The methylation vector and the transforming vector can also be transferred into *E. coli* BL21, which is deficient in dcm methyltransferase activity, but contains dam methyltransferase activity. The host environment methylates at the adenine N-6 position in the sequence GATC but not at the C-5 position of cytosine in the sequence CCWGG. High frequency transformation will rely on additional modifications to the transforming DNA.

Type I DNA methylation vectors can also be transformed with general replication and conjugative vectors. For example, the bacterial host cell is transformed with a homoacetogen methylation vector, such as pCOSMTI-2, pCOSMTI-1 or pCOSMTI-12, and an *E. coli*-Clostridial shuttle vector such as pACR-1 to generate a uniquely methylated transforming vector. As used herein a shuttle vector is a vector constructed so that it can propagate in two different host species. Therefore, DNA inserted into a shuttle vector can be tested or manipulated in two different cell types. For purposes of the present invention, the cell types are bacterial hosts expressing specific Type I methyltransferases that modify the DNA. The main advantage of these vectors is they can be manipulated in *E. coli* then used in a system which is more difficult or slower to use (e.g., other bacteria). In other embodiments the homoacetogen methylation vector, such as pCOSMTI-2, pCOSMTI-1 or pCOSMTI-12 are transformed with a conjugation vector such as pACC-1.

In particular embodiments the transforming DNA will be integrated into the bacterial recipient cell chromosome. In gene replacement transformations, modification of the transforming vector, which may or may not contain a replicon, would benefit from the instant invention.

The methylated DNA from the transforming factor can be purified from the bacterial host cell and transferred to a recipient cell that can degrade the plasmid DNA but which cannot degrade the methylated DNA. The purified DNA can be transferred to the recipient cell by methods of transformation, such as transduction, conjugation, and electroporation. As used herein a recipient cell is a bacterial cell into which exogenous methylated DNA is introduced.

Bacterial conjugation as relates to the present invention is the natural transfer of genetic material contained on plasmids between bacterial cells by direct cell-to-cell contact or by a bridge-like connection between two cells. It is a mechanism of horizontal gene transfer as are transformation and transduction although these two other mechanisms do not involve cell-to-cell contact. As used herein a donor cell is a bacterial cell that transfers DNA by conjugation to another bacterial cell.

Electroporation or electropermeabilization, is a significant increase in the electrical conductivity and permeability of the cell plasma membrane caused by an externally applied electrical field. It is usually used in molecular biology as a way of introducing some substance into a cell, such as loading it with a molecular probe, a drug that can change the cell's function, or a piece of coding DNA such as an expression vector.

Suitable transforming vectors contain an antibiotic resistance marker for selection in both the methylating bacterial host cell and the recipient bacterial cell along with a gram-negative or gram positive replicon and the cloned MtaseI-1 or the MtaseI-2 polynucleotide. The transforming vector can also include a transposon expressed in the bacterial recipient cell.

When methylation vectors are transformed with general replication and/or conjugative vectors, the vectors can be purified and transformed together into the bacterial recipient cell for additional protection upon entry into the recipient cell. As described above, the promoter in this embodiment is the Ppta-ack, which is highly expressed in both the host and recipient cells. Alternatively, the co-residing vectors may first be separated and then only the modified transforming vector transferred to the bacterial recipient cell.

The Examples which follow are illustrative of specific embodiments of the invention, and various uses thereof. They are set forth for explanatory purposes only, and are not to be taken as limiting the invention.

EXAMPLES

Genome Sequence Analysis

Analysis of the *C. coskatii* genome sequence was performed using the ERGO bioinformatics suite (Integrated Genomics, Arlington Heights, Ill.) and BLASTX. The analysis revealed genes involved in a complex restriction and modification system, which includes Type I, II, and III methyltransferases. Additionally, several methyl-directed endonucleases were identified. These systems target specific DNA sequences containing methylated adenines and cytosines followed by restriction.

Strains

*Clostridium autoethanogenum* strain DSM10061 [Abrini J, Naveau H, Nyns E-J, *Clostridium autoethanogenum*, sp. Nov. an anaerobic bacterium that produces ethanol from carbon dioxide. Arch. Microbiol. 1994, 4:345-351], *C. ragsdalei* P11 (ATCC BAA-622) [Hunhke R L, Lewis R S, Tanner R S: Isolation and characterization of novel Clostridial species. International patent 2008, WO 2008/028055], *C. coskatii* PS-02 (ATCC-PTA10522) [Zahn J A, Saxena J: Novel ethanologenic *clostridium* species, *Clostridium coskatii*] US 2011/0229947, *E. coli* DH10B (Life Technologies, Carlsbad, Calif.; dam$^+$, dcm$^+$, mcrAB-mrr$^-$), *E. coli* BL21 (Life Technologies, Carlsbad, Calif.; dcm$^-$, dam$^+$, mcrAB mrr$^+$) and GM2163 (Fermentas, Vilnius; $r_k^-$ $m_k^-$) were used to differentially methylate DNA containing transforming vectors. *E. coli* COSMTI-1 is GM2163 containing pCOSMTI-1 and a transforming vector; *E. coli* COSMTI-2 is GM2163 containing pCOSMTI-2 and a transforming vector; and *E. coli* COSMTI-12 is GM2163 containing pCOSMTI-12 and transforming vector.

Media

*E. coli* was grown in LB medium which was composed of 10 g per liter tryptone, 5 g per liter of yeast extract and 10 g per liter NaCl. LB ampicillin medium was composed of LB medium containing filter sterilized 100 µg ampicillin sulfate per ml.

*E. coli* was grown on 2×YT agar which is composed of 16 g per liter tryptone, 10 g per liter yeast extract and 5.0 g per liter NaCl.

2×YT ampicillin (Ap), chloramphenicol (Cm), kanamycin (Kn), tetracycline (Tc), erythromycin (Em) plates were composed of 2×YT agar (1.5%) containing 100 µg (Ap), 25 µg (Cm), 50 µg (Kn), 10 µg (Tc) and 40 µg (Em) per ml of agar.

*C. coskatii* fermentation medium was made anaerobically from concentrated vitamin, mineral and metals stocks with the compositions shown in Tables 1 and 2a-d.

*C. coskatii* plating medium was composed of fermentation medium containing 5 g per liter fructose (filter-sterilized and added post autoclaving), 10 g per liter yeast extract and 15-20 g per liter agar.

TABLE 1

Fermentation Medium Compositions

| Components | Amount per liter |
|---|---|
| Mineral solution, See Table 2(a) | 25 ml |
| Trace metal solution, See Table 2(b) | 10 ml |
| Vitamins solution, See Table 2(c) | 10 ml |
| Yeast Extract | 0.5 g |
| Adjust pH with NaOH | 5.8 |
| Reducing agent, See Table 2(d) | 2.5 ml |

TABLE 2(a)

Mineral Solution

| Components | Concentration (g/L) |
|---|---|
| NaCl | 80 |
| $NH_4Cl$ | 100 |
| KCl | 10 |
| $KH_2PO_4$ | 10 |
| $MgSO_4 \cdot 7H_2O$ | 20 |
| $CaCl_2 \cdot 2H_2O$ | 4 |

TABLE 2(b)

Trace Metals Solution

| Components | Concentration (g/L) |
|---|---|
| Nitrilotriacetic acid | 2.0 |
| Adjust the pH to 6.0 with KOH | |
| $MnSO_4 \cdot H_2O$ | 1.0 |
| $Fe(NH_4)_2(SO_4)_2 \cdot 6H_2O$ | 0.8 |
| $CoCl_2 \cdot 6H_2O$ | 0.2 |
| $ZnSO_4 \cdot 7H_2O$ | 1.0 |
| $NiCl_2 \cdot 6H_2O$ | 0.2 |
| $Na_2MoO_4 \cdot 2H_2O$ | 0.02 |
| $Na_2SeO_4$ | 0.1 |
| $Na_2WO_4$ | 0.2 |

TABLE 2(c)

Vitamin Solution

| Components | Concentration (mg/L) |
|---|---|
| Pyridoxine•HCl | 10 |
| Thiamine•HCl | 5 |
| Riboflavin | 5 |
| Calcium Pantothenate | 5 |
| Thioctic acid | 5 |

TABLE 2(c)-continued

Vitamin Solution

| Components | Concentration (mg/L) |
|---|---|
| p-Aminobenzoic acid | 5 |
| Nicotinic acid | 5 |
| Vitamin B12 | 5 |
| Mercaptoethanesulfonic acid | 5 |
| Biotin | 2 |
| Folic acid | 2 |

TABLE 2(d)

Reducing Agent

| Components | Concentration (g/L) |
|---|---|
| Cysteine (free base) | 40 |
| $Na_2S \cdot 9H_2O$ | 40 |

Example 1

Identification and Characterization of Methyltransferase MTI-1

MTI-1 Type I Methyltransferase was identified as part of a 7.33 kb operon containing the restriction subunits (R), specificity (S) and methylation (M) genes. The nucleotide sequence (SEQ ID NO: 1) and deduced amino acid sequence (SEQ ID NO: 2) of the *Clostridium coskatii* MTI-1 Type I methyltransferase are shown in FIGS. 1A and 1B. The MTI-1 coding sequence is 1419 bp including the stop codon. The DNA and deduced amino acid sequences of MTI-1 Type I methyltransferase were compared to protein sequences using BLASTX. The best match was to a Type I N-6 methyltransferase from *C. ragsdalei* (98% identity); other proteins with significant sequence identity were the N-6 DNA methyltransferase from *Clostridium carboxidivorans* P7 ZP05395073.1 (86% identity) and to an N-6 adenine-specific DNA-methyltransferase from *Clostridium cellulovorans* 743B YP 003842639.1 (85% identity). The major protein motif was to hsdM-adoMET over about 75% of the translated protein.

Example 2

Identification and Characterization of Methyltransferase MTI-2

MTI-2 Type I Methyltransferase was identified as part of a 6.887 kb operon containing the restriction subunits (R), specificity (S) and methylation (M) genes. The nucleotide sequence (SEQ ID NO: 3) and deduced amino acid sequence (SEQ ID NO: 4) of the *Clostridium coskatii* MTI-2 Type I methyltransferase are shown in FIGS. 2A and 2B. The coding sequence is 1446 bp including the stop codon. The DNA and deduced amino acid sequences of the MTI-2 Type I methyltransferase were compared to protein sequences using BLASTX. The best match was to a Type I N-6 methyltransferase from *Clostridium Maddingley* (87% identity) ZP 11365985.1. The major protein motif was hsdM-adoMET over the majority of the translated protein.

Example 3

Synthesis and construction of methyltransferase MTI-1 vectors

The 1419 bp open reading frame encoding MTI-1 along with a 296 bp promoter region Pptaack and 227 bp downstream of the gene were synthesized. The coding sequence was operably linked to the Pptaack promoter region and included a standard ribosome-binding site located 12 bp upstream from the translational start site. This promoter has been shown to be constitutively expressed at high levels in *E. coli* using promoterless antibiotic resistance genes. Gene synthesis was performed by Life Technologies/Gene Art Josef-Engert Str. II 93053 Regensburg Germany. The methyltransferase sequences were amplified by high-fidelity PCR, constructed in *E. coli* replicating vectors, subcloned and end-ligated to remove any overhangs to generate a clean sequence. After construction of the complete 1.942 kp expression cassette the sequence was verified using an ISO 9001:2008-certified quality management system and Applied Biosystems Genetic Analyzers. Synthesized expression DNA containing the MTI-1 polynucleotide was ligated into a M19-pUC-based vector with suitable engineered sites at the 5' end for downstream cloning and was designated pAC80. To allow co-residency with pMB1 replicons, the 1.942 kb MTI-1 cassette was released by HindIII digestion of pAC80, gel purified using the Qiaex kit (Qiagen, Hilden Germany) and ligated to calf-alkaline phosphotased pACYC184 that was previously digested with HindIII. Ligation mixtures were electroporated into competent *E. coli* DH10B host cells. Recombinant clones were selected on 2×YT agar plates containing tetracycline (5 µg/ml) and chloramphenicol (25 µg/ml). Recombinants were screened with HindIII for the inserted MTI-1 expression cassette sequence. The final methyltransferase construct is shown in FIG. 4 and was designated pCOSMTI-1.

Example 4

Synthesis and Construction of Methyltransferase MTI-2 Vectors

Figure 5:
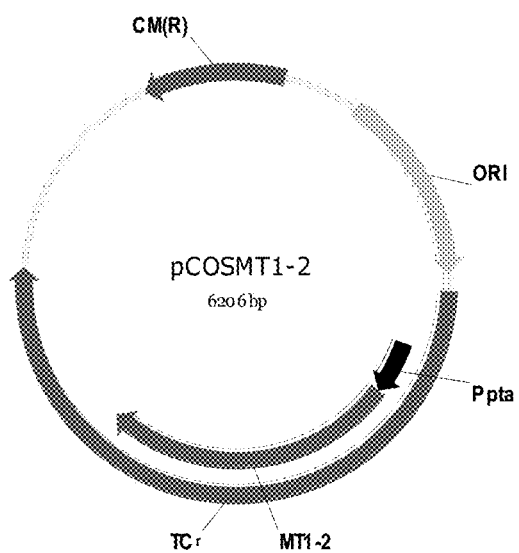
Figure 6:
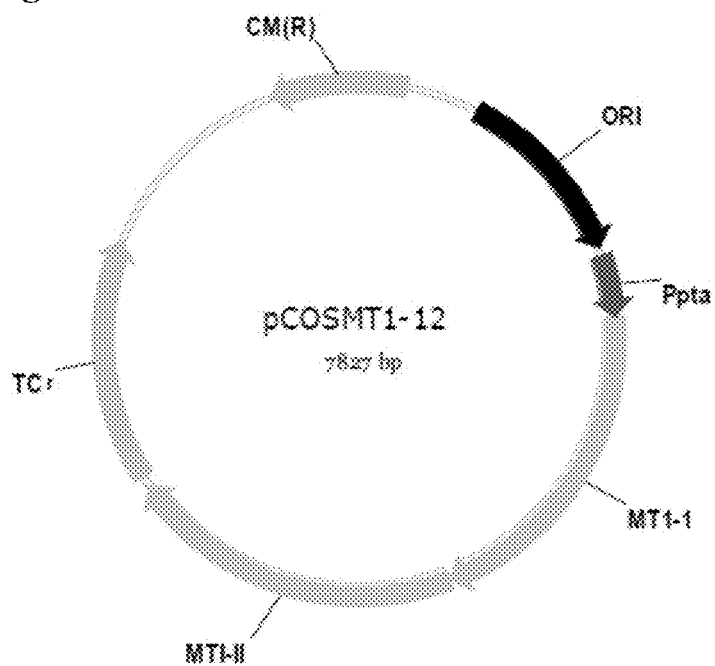

The 1446 bp open reading frame encoding MTI-2 along with the 296 bp promoter region and 233 bp downstream from the MTI-2 gene were synthesized. The coding sequence was operably linked to the Pptaack promoter as described in Example 3. Gene synthesis was performed by Life Technologies/Gene Art Josef-Engert Str. II 93053 Regensburg Germany. After construction of the complete 1.975 kp expression cassette the sequence was verified using an ISO 9001:2008-certified quality management system and Applied Biosystems Genetic Analyzers. Synthesized DNA was subcloned into a M19/pUC-based vector with suitable engineered sites at the 5' end for later cloning steps. This vector was designated pAC82. As described in Example 3, to allow co-residency with pMB1 replicons, the 1.975 kb cassette containing the Pptaack-MTI-2 polynucleotide in pAC82 was digested with BamHI and ligated to calf-alkaline phosphotased pACYC184 previously digested with the same enzyme. Clones were initially selected on 2×YT agar plates supplemented with chloramphenicol (25 µg/ml) and counter-selected on tetracycline (5 µg/ml) plates to verify sensitivity. Recombinant *E. coli* clones that displayed chloramphenicol resistance and tetracycline sensitivity were screened further by restriction analysis. Clones were screened using BamHI, HindIII and EcoRI and those that displayed the predicted restriction pattern confirmed the cloned Pptaack-MTI-2 cassette and were used in later experiments. The construct is shown in FIG. 5 and was designated pCOSMTI-2.

Example 5

Synthesis and Construction of Methyltransferase pCOSMTII-1 Vector

The 1671 bp open reading frame encoding *C. coskatii* MTII-1 (identified as greater than 90% DNA sequence conserved in *C. autoethanogenum, C. ljungdahlii,* and *C. ragsdalei*) along with a 296 bp promoter region (Ppta-ack) and 231 bp downstream of the *C. coskatii* gene were synthesized. The coding sequence was operably linked to the Pptaack promoter region and included a standard ribosome-binding site located 12 bp upstream from the translational start site as described above for the other Type I methyltransferase expression vectors. Gene synthesis was performed by Life Technologies/Gene Art Josef-Engert Str. II 93053 Regensburg Germany as described previously. The methyltransferase sequences were amplified by high-fidelity PCR, constructed in *E. coli* replicating vectors, subcloned and end-ligated to remove any overhangs to generate a clean sequence. After construction of the complete 2.198 kp expression cassette the sequence was verified using an ISO 9001:2008-certified quality management system and Applied Biosystems Genetic Analyzers. Synthesized expression DNA containing the MTII-1 polynucleotide was ligated into a M19-pUC-based vector with suitable engineered sites at the 5' end for downstream cloning and was designated pAC81. To allow co-residency with pMB1 replicons, the 2.198 kb MTII-1 cassette was released by HindIII digestion of pAC81, gel purified using the Qiaex kit (Qiagen, Hilden Germany) and ligated to calf-alkaline phosphotased pACYC184 that was previously digested with HindIII. Ligation mixtures were electroporated into competent *E. coli* DH10B host cells. Recombinant clones were selected on 2×YT agar plates containing tetracycline (10 μg/ml) and chloramphenicol (50 μg/ml). Recombinants were screened with HindIII for the inserted MTII-1 expression cassette sequence. The final methyltransferase construct is shown in FIG. 10 and was designated pCOSMTII-1.

Example 6

Construction of pCOSMTI-12

Vector pCOSMTI-12 is an *E. coli* replicating vector containing both MTI-1 and MTI-2 Clostridial Type I methyltransferases expressed from an operably-linked Clostridial promoter. Vector pCOSMTI-12 was generated using pAC80 and pAC82 as source DNA. A HindIII site located immediately downstream of the MTI-1 ORF was used as the cloning site for insertion of the MTI-2 Type I methyltransferase polynucleotide. Vector pAC80 was digested with HindIII (Fermentas, Vilnius) and the 5' ends dephosphorylated with fast calf alkaline phosphatase (Fermentas, Vilnius) according to the manufacturer's instructions. After enzyme digestion, the dephosphorylated vector was purified using the Qiaex kit. Vector pAC82 was digested with HindIII to release the 1.715 kb MTI-2 polynucleotide and gel purified using the Qiaex kit. After gel purification, the MTI-2 polynucleotide was ligated to pAC80 using rapid T4 DNA ligase (Fermentas, Vilnius) according to the manufacturer's instructions. Ligation mixtures were purified using isopropanol precipitation (at 0.8 volume) at −20° C. for 1 hour, centrifuged at room temperature at 12,000×g in a microfuge, and followed by a 70% ethanol wash to dry the DNA. Ligated DNA was resuspended in 10 μl of Tris buffer, pH 8.0. Electrocompetent *E. coli* DH10B was transformed with 1 μl of the ligation mix at 2.5 kV and transformants were selected on 2×YT agar plates for tetracycline and chloramphenicol resistance as described in Example 5. A control dephosphorylation reaction using calf-alkaline phosphatased-pAC80 was performed since the inserted DNA did not generate a selectable phenotype. Tetracycline- and chloramphenicol-resistant transformants were screened after plasmid miniprep purification using the Fermentas GeneJet kit. Recombinant vectors were screened by restriction digestion using BamHI and HindIII and confirmed clones were used in later experiments. Additionally, all recombinant vectors used for transformation experiments were sequence verified. The final construct is shown in FIG. 6 and was designated pCOSMTI-12.

Example 7

Construction of Broad-Host Range Methyltransferase Vectors

Methyltransferase genes are also cloned into a broad-host range vector to expand the range of hosts from which plasmid DNA can be retrieved and electrotransformed and mobilized into Clostridial hosts. For cloning the MTI-1 polynucleotide into the broad-host range plasmid pBBR1 an EcoRI digestion is performed on pAC80 to release the MTI-1 "cassette" containing Ppta-ack operably linked to the MTI-1 polynucleotide and ligated to EcoRI-digested pBBR1 using T4 DNA ligase (Fermentas), which is dephosphorylated with calf-alkaline phosphatase using 1 unit of phosphatase for 10 minutes. The ligation proceeds for 10 minutes using rapid DNA ligase and the ligation mixture is purified using the Qiaex kit. One microliter of the ligation mixture is used to transform *E. coli* DH10B with selection for chloramphenicol resistance. Recombinant plasmids are identified after replica patching onto 2×YT agar medium containing chloramphenicol or thiamphenicol (25 μg per ml of agar) and kanamycin sulfate (50 μg per ml agar). *E. coli* strains which display a thiamphenicol-resistant, kanamycin-sensitive phenotype are purified and further characterized by restriction digestion and sequencing for confirmation. One such plasmid, pBBRMTI-1, can be used in transformation and conjugation experiments.

For cloning the MTI-2 polynucleotide cassette into pBBR1, a similar procedure is used except the methyltransferase cassette is released from pAC82 using PstI and cloned into a unique PstI site on a modified pBBR-1. The PstI site is made unique by previously releasing a 1.240 kb PstI fragment containing the entire kanamycin resistance gene and surrounding sequences and religating the large 4.060 kb fragment to form ΔKnpBBR1. Plasmid ΔKnpBBR1 is digested with PstI and dephosphorylated with calf alkaline phosphatase and ligated to a 1.975 kb PstI fragment containing the MTI-2 cassette including the Pptaack from pAC82. The ligation proceeds for 10 minutes using rapid DNA ligase and is purified using the Qiaex kit. Transformation of *E. coli* DH10B cells is performed using 1 μl ligation mixture with selection on 2×YT agar medium containing thiamphenicol at 25 μg/ml 2×YT agar medium. Thiamphenicol-resistant strains are screened by restriction digestion using PstI. After restriction digestion screening of ten colonies and sequence confirmation across the MTI-2 gene six such plasmids are isolated and designated pBBRMTI-2. One such plasmid is used in transformations and conjugations.

For cloning both MTI-1 and MTI-2 Type I methyltransferase polynucleotide located on pCOSMTI-12 and operably linked to Ppta-ack, a BamHI digest of pCOSMTI-12 is performed to release a 3.657 kb fragment. The fragment is blunted using T4 DNA polymerase (Fermentas) according to the manufacturer's instructions. Plasmid pBBR1 is digested with SmaI and dephosphorylated with calf-alkaline phosphatase as described above. The 3.657 kb Type I methyltransferase gene cassette is gel purified and ligated to SmaI-digested pBBR1 using rapid T4 DNA ligase. Ligation mixtures are purified and transformed into electrocompetent E. coli DH10B cells and selected on 2×YT agar plates containing thiamphenicol (25 µg per ml 2×YT agar). Candidate recombinants are replica patched onto 2×YT medium containing kanamycin at 50 µg per ml agar and incubated overnight at 37° C. Strains that displayed a Thiamphenicol-positive, kanamycin-sensitive phenotype are further analyzed by restriction digestion and sequencing. Putative recombinants are digested with BamHI and PstI and analyzed on a 0.8% agarose gel (1×TAE buffer). Four such recombinants containing the entire 3.657 kb methylatransferase cassette are confirmed and designated pBBRMTI-12 and will be used in transformation and conjugation experiments.

Example 8

Construction of Shuttle Vector pACR-1

Figure 7A:
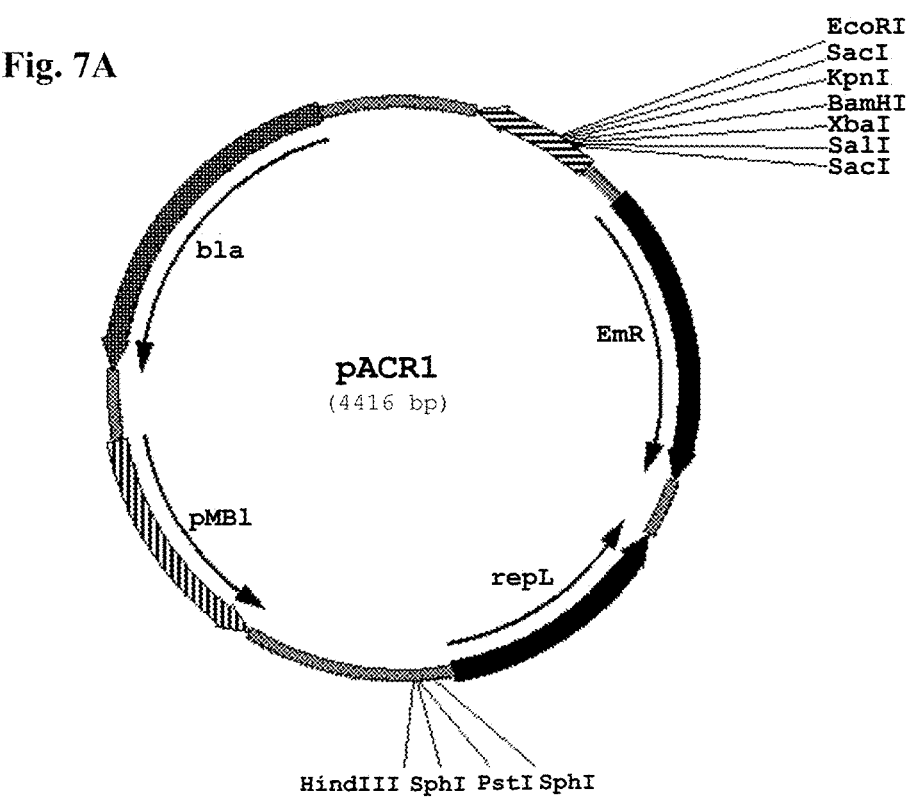
Figure 7B:
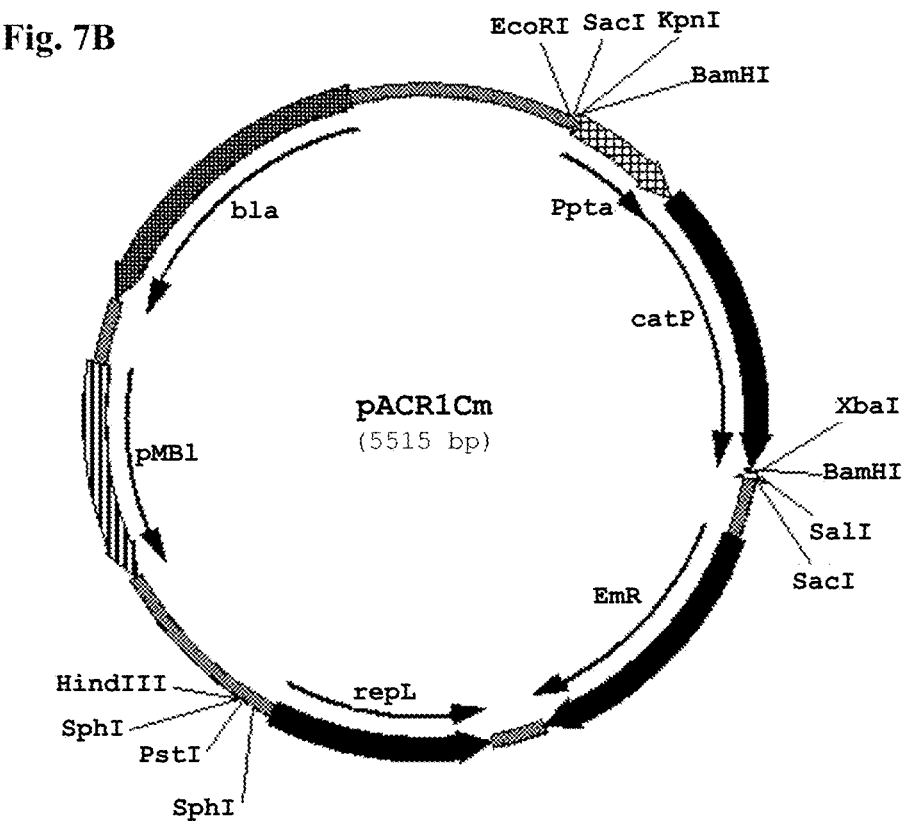

Vector pACR-1 is an *E. coli-Clostridium* shuttle vector containing cross-functional replicons and antibiotic markers. Vector pUC19 was digested with SalI and dephosphorylated with calf-alkaline phosphatase as described in previous Examples. After enzymatic treatment the plasmid DNA was precipitated with isopropanol (0.6-1.0 volume) and placed at −20° C. for 1 hour. DNA was pelleted at 12,000×g for 10 minutes in a minicentrifuge and washed with ice cold 70% ethanol and dried. The DNA pellet was resuspended in 30 µl of Tris buffer pH 8.0. A 1.730 kb SalI-PstI fragment contained on a pMB1 replicating vector (pGEM T easy, Promega, Madison Wis.) containing replicon repL and an erythromycin resistance gene (an origin of replication and antibiotic resistance gene that both function in *Clostridia*) originally derived from pE194 (Weisblum et al., 1979, *Journal of Bacteriology*, Plasmid copy control: Isolation and characterization of high-copy-number mutants of plasmid pE194, 137:635-643) was ligated to pUC19 using rapid T4 DNA ligase. After transformation and selection, vectors were screened and confirmed by restriction analysis and sequencing junction regions. This general *E. coli-Clostridium* shuttle vector was designated pACR1 (FIG. 7A). Alternative antibiotic selection markers were generated by cloning separately tetracycline (originally derived from pACYC184), chloramphenicol (originally derived from pACYC184) and kanamycin (originally derived from Tn5) resistance genes expressed from a clostridial promoter (Psadh), into unique sites located in the multiple cloning region contained in the vector. After purification, ligation mixtures were transformed into DH10B electrocompetent *E. coli* with selection for dual antibiotic resistance. This generated a series of versatile selection vectors based on the repL origin and dual *Clostridium* antibiotic selection markers along with erythromycin resistance, which has been successfully used in a wide variety of *Clostridia* (pACR1Cm, FIG. 7B).

Example 9

Construction of Conjugation Vector pACC-1

Figure 8A:
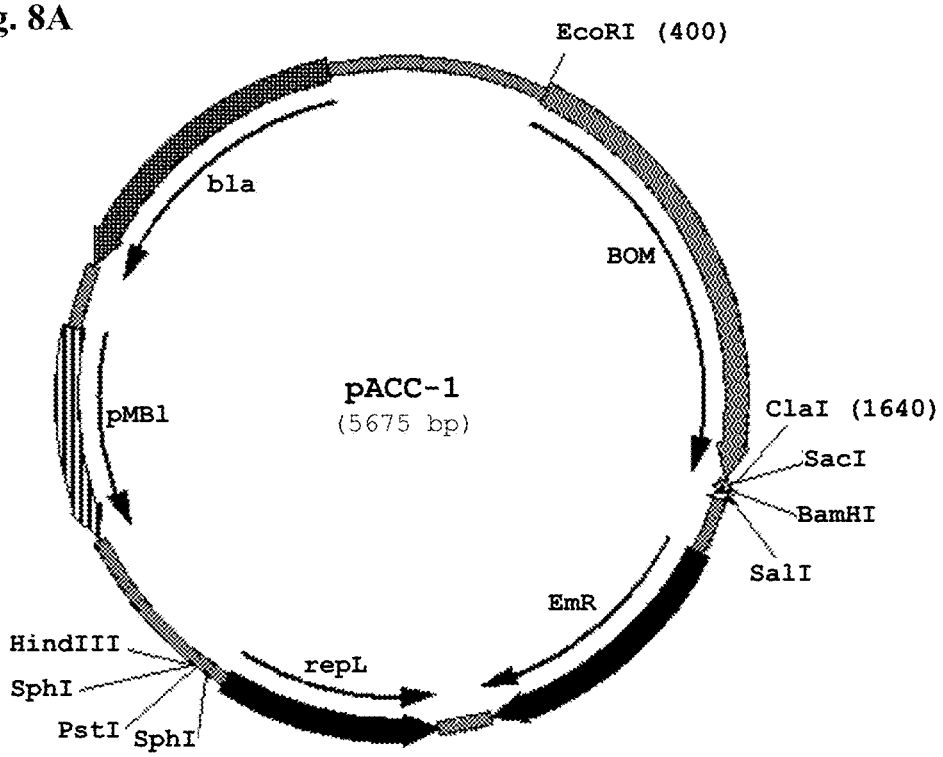

Vector pACC-1 is an *E. coli-Clostridium* conjugative vector containing mobilization and origin of transfer genes from RP4 and cross-functional antibiotic selection markers expressed from a Clostridial promoter. Plasmid pARO190 (Parke D, 1990, *Gene*, Construction of mobilizable vectors derived from plasmids RP4, pUC18 and pUC19 93(1): 135-137) was used as the starting vector since it contains the basis for mobilization region and origin of transfer (BOM) along with a convenient multiple cloning site. Plasmid pARO190 was digested with SalI and dephosphorylated with rapid calf alkaline phosphatase for 10 minutes at 37° C. After enzymatic treatment, the vector was purified by Qiaex kit and resuspended in 30 µl Tris buffer pH 8.0. One µl of this (~50 ηg) was used in dephosphorylation control tests. Additionally, pARO190 has the lacZα complementation fragment so blue/white screening was used in the initial cloning step. The 1.730 kb fragment containing repL and the erythromycin resistance gene (Em) was released with SalI, gel purified and ligated to SaiI-digested dephosphorylated pARO190 using T4 DNA ligase for 10 minutes at room temperature. After terminating and purifying the ligation reaction with the Qiaex kit, the ligation mixture was resuspended in 30 µl of Tris buffer pH 8.0. One µl of ligation mixture was electroporated into DH10B electrocompetent cells and plated on 2×YT agar containing ampicillin at a concentration of 100 µg per ml agar medium. The blue-white indicator X-gal (5-bromo-4-chloro-3-indolyl-beta-D-galactopyranoside) was added to the 2×YT agar at a final concentration of 20 µg per ml to screen for plasmids containing inserts. After purifying plasmids from five white colonies, restriction analysis was performed to verify insertion of the repL-Erm genes. Sequencing was also performed using the mp19/pUC19 universal and reverse primers that span the multiple cloning region to confirm the integrity of the cloned sequence. This construct was designated pACC-1 (FIG. 8A).

Figure 8B:
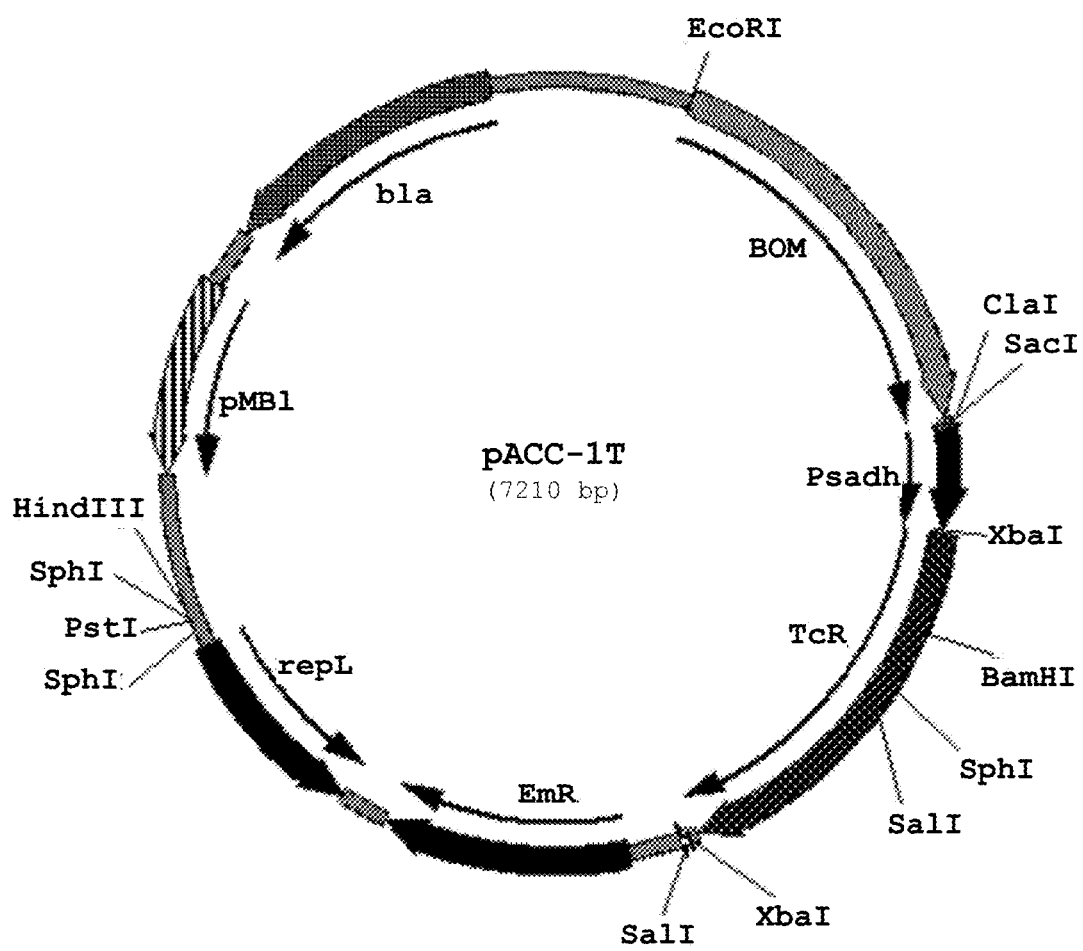

To impart additional cross-functional antibiotic resistances and generate a series of versatile *E. coli-Clostridium* conjugative vectors additional antibiotic resistance markers were ligated into pACC-1 in the multiple cloning site as described in Example 6. In all cases, the antibiotic resistance markers were expressed from a strong clostridial promoter, Psadh, and were cloned into either the EcoRI, BamHI, or XbaI sites. The antibiotic resistance marker cassettes were released using the appropriate enzyme from pGEM T easy-cloned PCR products, gel purified using a Qiaex kit and ligated to dephosphorylated pACC-1 using rapid T4 DNA ligase. After ligation and purification, the mixture was electroporated into electrocompetent DH10B cells with selection on ampicillin and the selectively expressed antibiotic. Vector pACC-1 containing the TcR gene expressed from a clostridial promoter is shown in FIG. 8B. In those cases where replication was not desirable (i.e., generation of a conjugative suicide vector) the 1.730 kb repL-Em cassette was deleted from the appropriate pACC-1-based vector using SalI and religated using T4 DNA ligase. These vectors were also modified to contain homologous DNA for integration into the host chromosome.

Example 10

Transformation of the Methylation Vectors into *E. coli*

Vector constructs pCOSMTI-1, pCOSMTI-2, pCOSMTI-12, were transformed into *E. coli* host strains with varying restriction-modification systems. Genotypically R/M variable, commercial strains contain one or more mutations in the four R/M systems known to exist in *E. coli*. *E. coli* DH10B (Life Technologies, Carlsbad, Calif.) contains mutations in the mcrABmrr and hsd systems. *E. coli* BL21 contains mutations in the dcm system. *E. coli* DH5α-e is positive for all systems except the hsdB system. *E. coli* ER2275 has a similar genotype as DH10B with regard to its restriction-modification systems. *E. coli* strain GM2163 is R/M negative.

Vectors pCOSMTI-1, pCOSMTI-2, pCOSMTI-12, and pCOSMTII-1 (as control) were separately electrotransformed into *E. coli* BL21, DH10B, DH5α-e, GM2163 and ER2275 using 0.1 cm gap cuvettes maintained at 4° C. and 20 µl of cells with selection on 2×YT agar plates containing chloramphenicol at 25 µg per ml of agar.

Example 11

Generation of *E. coli* Methyltransferase Strains for Testing in *Clostridia* spp.

Figure 9:
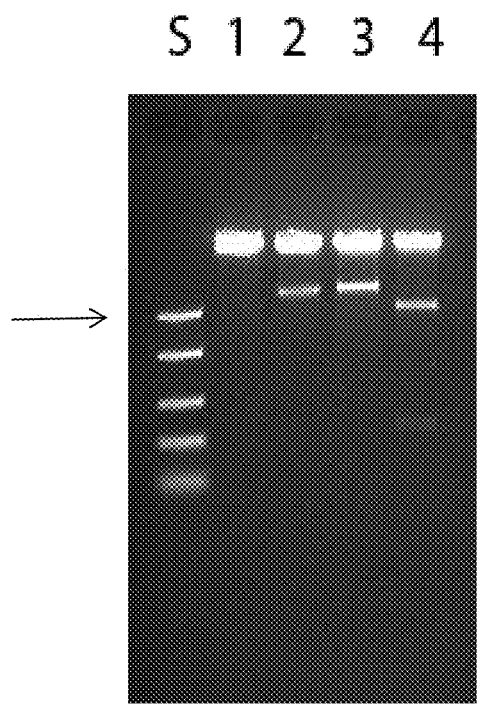
Figure 10:
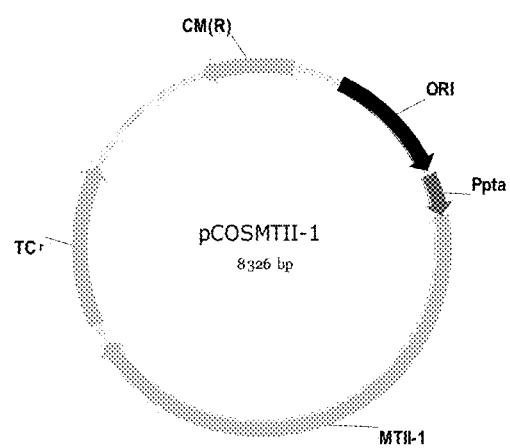

The *E. coli* host strains BL21, DH10B, DH5α-e, GM2163 and ER2275 containing the methylation vectors, pCOSMTI-1, pCOSMTI-2, pCOSMTI-12, pMTII-1 were made electrocompetent according to the method described in Sambrook et al (In: Molecular cloning: a laboratory manual, 1987. J. Sambrook, E. F. Fritsch, T. Maniatis. Sambrook, J.). Vectors pACR-1 and the pACC-1 series are compatible with vectors pCOSMTI-1, pCOSMTI-2, pCOSMTI-12, pMTII-1 and can co-reside in the same cell with appropriate antibiotic selection (FIG. 9). FIG. 9 shows co-residency of two such co-resident vector *E. coli* strains containing pCOSMTI-12 and pACR-1 and pCOSMTI-12 and pACC-1ET. After electrotransformation and purification of vectors from four different *E. coli* hosts a 1.2% Tris-Borate-EDTA (TBE, pH 8.0) gel was run to resolve vectors after restriction digestion with BamHI or HindIII. *E. coli* DH10B was transformed with pACR-1 only, with pACR-1 in a host containing pCOSMTI-12, with pACC-1 in a host already containing pMTI-1 and with a host already containing pCOSMTI-12. These strains were selected on 2×YT agar containing either ampicillin (100 µg per ml) only or ampicillin (50 µg per ml) in combination with tetracycline (10 µg per ml). BamHI-digested plasmid from an *E. coli* strain containing only pACR-1 showed one large bright band (FIG. 9, lane 1). Plasmid DNA digested with HindIII from *E. coli* containing pACR-1 and pCOSMTI-12 (FIG. 9, lane 2) showed the expected 1.942 kb fragment containing the Ppta-MTI-1 cassette. As expected, the 1.942 kb band is much less bright than pACR-1, since the methylation vector is approximately $\frac{1}{40}^{th}$ the copy number of pACR-1. Plasmid DNA digested from *E. coli* co-residing pACC-1 and pCOSMTI-1 was digested with BamHI and the expected 1.942 kb band containing the Ppta-MTI-1 cassette was observed along with the larger remaining parts of the vectors (FIG. 9, lane 3). Digesting plasmid DNA from the *E. coli* host containing pACC-1 and pCOSMTI-12 with HindIII yielded the expected bands of 1.446 kb and 0.225 kb from the methylating vector pCOSMTI-12 along with the remaining parts of the vectors (compressed in the TBE gel). These bands were also significantly less bright than the conjugative vector pACC-1.

These results as well as others consistent with these data observed in the other *E. coli* R/M variable hosts described in Example 8 confirmed the stable co-residency of the Type I methyltransferase containing vectors with the general replication and conjugative vectors. All these *E. coli* host strains served as the source for differentially methylated plasmid DNA for electrotransformation or conjugative transfer into recipient Clostridial host strains.

Example 12

Electrotransformation of *C. autoethanogenum* with Type 1-Methylated Plasmid DNA Transformation experiments were performed in order to determine the effects of methylated DNA on gene transfer and stable replication in *C. autoethanogenum* and other solventogenic *Clostridia*. Plasmid DNA was quantified and desalted using 100 kDa UF filters (Millipore, Bedford Mass.) and a 40-fold volume of 10 mM Tris buffer pH 8.0. For each electrotransformation 1-3 µg of DNA was used and transferred to an ice-cold 0.2 cm gap cuvette containing 50 µl of electrocompetent *C. autoethanogenum, C. ragsdalei* and *C. coskatii* previously frozen at −80° C. according to the method described by Leang et al. (Leang et al. 2012, *Applied and Environmental Microbiology*, Epub ahead of print 30 Nov. 2012) with minor modifications. Cells were maintained in SMP buffer (270 mM sucrose, 1 mM $MgCl_2$, 7 mM sodium phosphate, pH 6.1) with 15% DMSO added when stored at −80° C. until use.

Electrocompetent cells were prepared from single colony isolates grown on fermentation medium (Tables 1 and 2) containing 0.5% fructose and 10 g per liter yeast extract. Cells were initially grown in 5 ml of fermentation medium in anaerobic Balch tubes with a headspace of $N_2CO_2H_2$ (80:15:5) for 48 hours and transferred three times in 150 ml serum bottles containing 20 ml fermentation medium containing 40 mM DL-threonine with a consistent gas phase. Cells were harvested anaerobically at early and mid-log phase of growth ($OD_{600}$ nm 0.3 to 0.7) at 3225×g for 20 minutes, washed with SMP buffer 2 times and concentrated 100-fold before freezing. Competent cells were rapidly frozen in an alcohol bath maintained at −80° C. For electrotransfer into competent Clostridial cells 1 µg of methylated DNA was added and mixed. Electroporation was carried out in a Bio-rad Excel electroporator (Bio-rad, Hercules Calif.) set to 25 µF, 600Ω, 1.5-2.5 kV. After electroshock, cells were immediately resuspended in warmed fermentation medium and transferred to anaerobic Balch tubes containing 4 ml fermentation medium for recovery overnight. The next day, after some perceptible change in OD was observed, cells were pelleted at 10,000×g in a microfuge and plated on fermentation medium agar supplemented with 0.5% fructose and the appropriate antibiotic for selection of transformants. Control experiments using unmethylated DNA were performed alongside experiments using DNA methylated with the two Clostridial Type I methylation vectors and a control Type II methyltransferase expression vector, pCOSMTII-1.

Example 13

Gene Transformation of Wild-Type *C. autoethanogenum* Using Type I-Methylated DNA Electroporation experiments were performed to determine whether methylated DNA would increase DNA transformation frequency above levels observed with unmethylated DNA. *E. coli* XL1-Blue strains were electrotransformed with the *E. coli-Clostridium* shuttle vector pACR1 and either pCOSMTI-1, pCOSMTI-2, pCOSMTI-12, or pCOSMTII-1 to generate a series of co-residing plasmid vector strains. Selection for co-residing plasmids in *E. coli* was done on LB agar medium (Sambrook et al. 1989) containing erythromycin at 50 µg/ml and tetracycline at 10 µg/ml. After overnight growth at 37° C. on the selective medium, three individual colonies were grown in liquid medium and screened by restriction analysis to confirm co-residency of the methylating vector and the *E. coli-Clostridium* shuttle vector. After confirmation of stable plasmid co-residence a large-scale culture was made to generate DNA for electrotransformation into wild-type *C. autoethanogenum*. The *C. coskatii* methyltransferases contained in plasmids pCOSMTI-1, pCOSMTI-2 and pCOSMTII-1 were used in electrotransformations of *Clostridium* as described in Examples 10 and 11. An *E. coli* host strain containing replicating pACR1 only was used as an unmethylated DNA control. Electroporations without any added plasmid DNA additions acted as negative DNA controls.

Table 3. shows the results of gene transfer experiments using plasmids pCOSMTI-1, pCOSMTI-2, pCOSMTII-I and pACR1. pACR1 alone showed a transformation frequency of about 135 CFU/µg. When Type I methyltransferase MTI-1 was used to methylate pACR1 a slightly higher number of CFU/µg was observed (Table 3). Using DNA methylated by MTI-2 showed an almost 10-fold increase in transformation frequency (Table 3). The Type II methyltransferase MTII-1 didn't show any difference in transformation frequency when compared to the unmethylated DNA control vector, pACR1.

| Plasmid | CFU/plate | DNA(µg)[a] | Frequency[b] |
|---|---|---|---|
| pACR1 | 325 | 3 | 135 CFU/µg |
| pCOSMTI-1 | 384 | 3 | 160 CFU/µg |
| pCOSMTI-2 | 3201 | 3 | 1333 CFU/µg |
| pCOSMTII-1 | 285 | 3 | 118 CFU/µg |
| ND | — | 0 | 0 |

[a]represents the total amount of shuttle vector and methylating vector DNA;
[b]represents the total CFU generated from transfer and replication of shuttle vector only.

Example 14

Transfer of Type I-Methylated DNA into *C. autoethanogenum* and Other Solventogenic *Clostridia* by Conjugation The effect of methylated DNA on conjugal transfer was tested with and without using the helper *E. coli* strain S-17 containing pACC-1ET and pCOSMTI-12, pACC-1ET and pCOSMTI-1 and pACC-1ET and pCOSMTI-2 separately to test for the individual contributions of the methyltransferases on conjugal gene transfer efficiency. *E. coli* S-17 contains chromosomal functions that assist in the conjugal transfer of DNA in a bi-parental mating. This has been shown to improve conjugal transfer up to 5-10 fold versus using a triparental mating scheme. In those cases where a more variable methylation pattern was desired, tri-parental matings were performed with an *E. coli* helper strain, *E. coli* pCOSMTI-12 and the Clostridial recipient host. Once the *E. coli* strains were confirmed to contain stable co-resident vectors in the S-17 cells, conjugation experiments were performed. *C. autoethanogenum* was grown in anaerobic fermentation medium as described in Example 10. Before the filter mating procedure, the culture was transferred three times at early log phase (OD 600 nm 0.3) before harvesting and mixing with *E. coli*. For conjugations, *E. coli* was grown in LB medium with maintenance levels of ampicillin and tetracycline (10 µg per ml ampicillin and 1 µg per ml tetracycline) to an $OD_{600nm}$ of 0.5. *C. autoethanogenum* and other solventogenic *Clostridia* were grown to an $OD_{600nm}$ of between 0.3 and 0.7 when mixed with an equal volume of *E. coli* based on cell counts. If the optical densities were slightly different from previously established cell counts relating to cells/ml of broth the volumes were adjusted accordingly. Mixtures of cells were pelleted by centrifugation at 1000×g and resuspended in liquid medium at an equivalent OD of 5 and plated on previously sterilized 0.22 µM filters (Millipore) on fermentation medium agar or RCM (Difco, Becton Dikinson, Franklin Lakes, N.J.) agar. Matings were allowed to proceed for 24 hours at 37° C. in an anaerobic jar (Oxoid) with an $N_2CO_2H_2$ (80:15:5) headspace. After 24 hours incubation, the cells were harvested into 1 ml of fermentation medium and dilutions up to $10^3$-fold were spread onto fermentation agar containing 0.5% fructose containing 10 µg per ml tetracycline for selection of the *Clostridium* and 2 µg per ml nalidixic acid and trimethoprim to counterselect *E. coli*. Conjugation frequencies were calculated and compared to experiments using unmethylated DNA.

```
SEQ ID NO: 1: Polynucleotide sequence of MtaseI-1
ATGAATACACAGGAAATAGTAAGCAAACTTTGGAACCTTTGTAACGTACTAAGAGA

TGATGGAATAACTTATCATCAATATGTAACAGAATTAACATATATTCTTTTCTTAAA

GATGGCAAAGGAAACAGGTACAGAGGATAAATTGCCAGAAGGTTATAGATGGGAT

GATTTAAAAGTTTATAGAGGAATGGAACTTAAGAAATTTTATAATAAATTATTAAAT

TATCTTGGAGAAAAGACTACTGGGATAGTGCAAAAAATATATCAGGGATCTGCAAC

AAATATAGAAGAACCAAAAAATCTAGAAAAAATAATTAAAACTATAGATGGATTAG

ATTGGTATTCAGCAAAAGAAGAAGGACTTGGAAACTTATATGAAGGATTACTTGAA

AAAAATGCATCTGAGAAAAAATCTGGTGCAGGACAATACTTTACTCCAAGAGTATT

AATTAATGTTATGGTGGAACTTATTGATCCAAAACCAGGTGAAAAATGCAATGACCC

TGCAGCAGGAACCTTTGGATTTATGATTGCTGCAGATCGTTACATGAAACAGAAAC

AGACAACTATTTTGATTTAGGTACAGAACTTCAAGAGTTTCAGAGAACTAAGGCTTT
```

```
TTCTGGCTGTGAATTAGTTCACGAAACACATAGATTAGCCCTTATGAATGCTATGCT

TCATGATATAGAAGGAAACATAATCCTCGGAGATACTTTAACAAATACAGGAAAGC

AGATGAAAGACTTAAATGTTGTGCTTTCAAACCCTCCATTTGGAACTAAAAGAGGTG

GTGAAAGAGCAACAAGAGATGATTTGACTTACATGACTTCAAATAAACAATTAAAC

TTCTTGCAGCACATATATAGAAGTTTAAAAGCAGATGGAAAAGCAAGAGCAGCTGT

GGTATTGCCAGATAATGTACTATTTGATCATAATGATGGAGCGAAGATTCGTGCGGA

TTTAATGGATAAATGTAATCTACATACAATATTACGGTTACCTACTGGTATTTTCTAT

GCTAAAGGAGTTAAAACAAATGTGCTTTTCTTTACTAGAGGTACTAGTGATAAAGAC

AATACTAAAGAAGTTTGGATATATGATTTGCGTACCAATATGCCTAGCTTTGGAAAG

ACAAATCCTTTAAAGAAAGAGCATTTTGAAGACTTTATAAAGGCTTATACTTCTGAG

GATAGAACAAAGGTGAAAGATGAACGTTTTTCGGTATTTACTAGAGAAGAAATAAA

AGAGAAAAATGATAACCTTGACCTAGGTTTAATTCGTGATGAAAGTGTATTAGACTA

TGAAGATCTACAAGATCCAATTGAAAGTGGTGAAGAAATAACTTCACAACTTGAAG

AGGCAATGGATTTAATCCAAACTGTTGTAAAGAAACTAAAGATTTTAGGCGGTGAC

AGGTAA

SEQ ID NO: 2: Amino acid sequence of MtaseI-1.
M N T Q E I V S K L W N L C N V L R D D G I T Y H Q Y V T E L T Y I

L F L K M A K E T G T E D K L P E G Y R W D D L K V Y R G M E L K

K F Y N K L L N Y L G E K T T G I V Q K I Y Q G S A T N I E E P K N

L E K I I K T I D G L D W Y S A K E E G L G N L Y E G L L E K N A S

E K K S G A G Q Y F T P R V L I N V M V E L I D P K P G E K C N D P

A A G T F G F M I A A D R Y M K Q K T D N Y F D L G T E L Q E F Q

R T K A F S G C E L V H E T H R L A L M N A M L H D I E G N I I L G

D T L T N T G K Q M K D L N V V L S N P P F G T K R G G E R A T R

D D L T Y M T S N K Q L N F L Q H I Y R S L K A D G K A R A A V V

L P D N V L F D H N D G A K I R A D L M D K C N L H T I L R L P T G

I F Y A K G V K T N V L F F T R G T S D K D N T K E V W I Y D L R T

N M P S F G K T N P L K K E H F E D F I K A Y T S E D R T K V K D E

R F S V F T R E E I K E K N D N L D L G L I R D E S V L D Y E D L Q

D P I E S G E E I T S Q L E E A M D L I Q T V V K K L K I L G G D R

SEQ ID NO: 3: Polynucleotide sequence of Mtase I-2.
ATGTCAATAACAAACGTAGTAAAATCAGTACAAGATATAATGCGCCAGGATGCAGG

GGTAGATGGAGATGCTCAAAGAATATCTCAACTAGTTTGGATGATATTTTTAAAGGT

ATTTGATGCAAAAGAAGAGGAATGGGAATTAGAGTATGATGATTATACACCTATTA

TTCCAGAAGAATTGAGATGGAGCAACTGGGCTCAAGATGATGAAGGAATTACAGGC

GATGAGCTTTTAGACTTTGTAAACAATAAATTATTCAAAGGTTTAAAGGAAATGGAA

GTAGATGAGAATAGTGATGCTAAAGCTTTATTAGTTAAATCTGTATTTGAAGATTCC

TATAATTATATGAAATCAGGAGCTTTAATGAGGCAGGTAATAAATAAGTTAAATGA

AATAGATTTTACAGCAGGTGAAGACAGACATTTATTTAATGATATATATGAAAATAT

ATTAAAAGATCTTCAAAGTGCAGGCAATGCAGGAGAATTCTATACACCAAGACCTG

TTACACAATTTATAATAGATATGCTAAGTCCAAAGCTTGGTGAAAAAGTAGCTGACT

TTGCTTGTGGTACCGGTGGATTTTTAACATGTGCCATAGAAAACTTAAAAAAACAGG
```

-continued

```
AAACCAAAGTTGAAGATTTAAAAATATTAGGTGAAACCATAATGGGTGTAGAAAAG

AAACCGCTTCCTCACATGCTTGCTACAACTAACCTGATACTTCATGATATTGATGTGC

CAAACATAAAACATGATAATTCTTTGATGAAGAATGTAAGAGATTTAAAGCCTTCAG

AATATGTGGATGTAATAGCAATGAATCCTCCTTTTGGCGGAATTGAAGAAGATATGG

TACTAACTAATTTCCCTCAGCAGTTTCAAACAAAAGAAACAGCAGATTTATTTATGA

CTCTTATAATGTATAGATTAAGTGAAAAAGGAAGAGCGGGAGTAGTACTTCCAGAT

GGATTTTTATTTGGTGAAGGTGTAAAGACTCATATAAAAGAAAAACTTTTAAATGAA

TTTAACCTTCATACTATAGTAAGAATGCCTAATGGAGTATTTGCCCCATATACGGGA

ATAAATACAAACCTTTTATTCTTTGAAAAAGGTAAGCCAACAGAAGAAGTTTGGTTC

TTTGAACATCCACTTCCTGAAGGATATAAAAATTATACTAAAACCAAACCAATAAGA

TATGAAGAATTTGAACTGGAGAAGAAGTGGTGGAATAACAGAGAAGAAAATGAGT

ATGCGTGGAAGGTTTCAGTAGAGGACATTAAAAATAGAAATTATAATTTAGATTATA

AAAATCCTAATAAGGAAGAAGAAGATTTAGGAGATCCAAAGGCATTATTAAAAAAA

TATCATGAAGCTGCTGCTGATGTAGATAAATTGCAAGATTCTTTGATAGATGAATTA

AAGAAGATTTTAGAAGGGACATCAAAATAG

SEQ ID NO: 4: Amino acid sequence of Mtase I-2.
M S I T N V V K S V Q D I M R Q D A G V D G D A Q R I S Q L V W M

I F L K V F D A K E E E W E L E Y D D Y T P I I P E E L R W S N W A

Q D D E G I T G D E L L D F V N N K L F K G L K E M E V D E N S D

A K A L L V K S V F E D S Y N Y M K S G A L M R Q V I N K L N E I

D F T A G E D R H L F N D I Y E N I L K D L Q S A G N A G E F Y T P

R P V T Q F I I D M L S P K L G E K V A D F A C G T G G F L T C A I

E N L K K Q E T K V E D L K I L G E T I M G V E K K P L P H M L A T

T N L I L H D I D V P N I K H D N S L M K N V R D L K P S E Y V D V

I A M N P P F G G I E E D M V L T N F P Q Q F Q T K E T A D L F M T

L I M Y R L S E K G R A G V V L P D G F L F G E G V K T H I K E K L

L N E F N L H T I V R M P N G V F A P Y T G I N T N L L F F E K G K

P T E E V W F F E H P L P E G Y K N Y T K T K P I R Y E E F E L E K

K W W N N R E E N E Y A W K V S V E D I K N R N Y N L D Y K N P

N K E E E D L G D P K A L L K K Y H E A A A D V D K L Q D S L I D

E L K K I L E G T S K

SEQ ID NO: 5: Pptaack + Mtase I-1
TGATTGATTATTTATTTTAAAATGCCTAAGTGAAATATATACATATTATAACAATAA

AATAAGTATTAGTGTAGGATTTTTAAATAGAGTATCTATTTTCAGATTAAATTTTTGA

TTATTTGATTTACATTATATAATATTGAGTAAAGTATTGACTAGCAAAATTTTTTGAT

ACTTTAATTTGTGAAATTTCTTATCAAAAGTTATATTTTTGAATAATTTTTATTGAAA

AATACAACTAAAAAGGATTATAGTATAAGTGTGTGTAATTTTGTGTTAAATTTAAAG

GGAGGAAAATGAATACACAGGAAATAGTAAGCAAACTTTGGAACCTTTGTAACGTA

CTAAGAGATGATGGAATAACTTATCATCAATATGTAACAGAATTAACATATATTCTT

TTCTTAAAGATGGCAAAGGAAACAGGTACAGAGGATAAATTGCCAGAAGGTTATAG

ATGGGATGATTTAAAAGTTTATAGAGGAATGGAACTTAAGAAATTTTATAATAAATT

ATTAAATTATCTTGGAGAAAAGACTACTGGGATAGTGCAAAAAATATATCAGGGAT
```

-continued

CTGCAACAAATATAGAAGAACCAAAAAATCTAGAAAAAATAATTAAAACTATAGAT

GGATTAGATTGGTATTCAGCAAAAGAAGAAGGACTTGGAAACTTATATGAAGGATT

ACTTGAAAAAAATGCATCTGAGAAAAAATCTGGTGCAGGACAATACTTTACTCCAA

GAGTATTAATTAATGTTATGGTGGAACTTATTGATCCAAAACCAGGTGAAAAATGCA

ATGACCCTGCAGCAGGAACCTTTGGATTTATGATTGCTGCAGATCGTTACATGAAAC

AGAAAACAGACAACTATTTTGATTTAGGTACAGAACTTCAAGAGTTTCAGAGAACT

AAGGCTTTTTCTGGCTGTGAATTAGTTCACGAAACACATAGATTAGCCCTTATGAAT

GCTATGCTTCATGATATAGAAGGAAACATAATCCTCGGAGATACTTTAACAAATACA

GGAAAGCAGATGAAAGACTTAAATGTTGTGCTTTCAAACCCTCCATTTGGAACTAAA

AGAGGTGGTGAAAGAGCAACAAGAGATGATTTGACTTACATGACTTCAAATAAACA

ATTAAACTTCTTGCAGCACATATATAGAAGTTTAAAAGCAGATGGAAAAGCAAGAG

CAGCTGTGGTATTGCCAGATAATGTACTATTTGATCATAATGATGGAGCGAAGATTC

GTGCGGATTTAATGGATAAATGTAATCTACATACAATATTACGGTTACCTACTGGTA

TTTTCTATGCTAAAGGAGTTAAAACAAATGTGCTTTTCTTTACTAGAGGTACTAGTG

ATAAAGACAATACTAAAGAAGTTTGGATATATGATTTGCGTACCAATATGCCTAGCT

TTGGAAAGACAAATCCTTTAAAGAAAGAGCATTTTGAAGACTTTATAAAGGCTTATA

CTTCTGAGGATAGAACAAAGGTGAAAGATGAACGTTTTCGGTATTTACTAGAGAA

GAAATAAAAGAGAAAAATGATAACCTTGACCTAGGTTTAATTCGTGATGAAAGTGT

ATTAGACTATGAAGATCTACAAGATCCAATTGAAAGTGGTGAAGAAATAACTTCAC

AACTTGAAGAGGCAATGGATTTAATCCAAACTGTTGTAAAGAAACTAAAGATTTTA

GGCGGTGACAGGTAA

SEQ ID NO: 6: Pptaack + MtaseI-2
GATCCTGATTGATTATTTATTTTAAAATGCCTAAGTGAAATATATACATATTATAACA

ATAAAATAAGTATTAGTGTAGGATTTTTAAATAGAGTATCTATTTTCAGATTAAATTT

TTGATTATTTGATTTACATTATATAATATTGAGTAAAGTATTGACTAGCAAAATTTTT

TGATACTTTAATTTGTGAAATTTCTTATCAAAAGTTATATTTTTGAATAATTTTTATTG

AAAAATACAACTAAAAAGGATTATAGTATAAGTGTGTGTAATTTTGTGTTAAATTTA

AAGGGAGGAAAATGTCAATAACAAACGTAGTAAAATCAGTACAAGATATAATGCGC

CAGGATGCAGGGGTAGATGGAGATGCTCAAAGAATATCTCAACTAGTTTGGATGAT

ATTTTTAAAGGTATTTGATGCAAAAGAAGAGGAATGGGAATTAGAGTATGATGATT

ATACACCTATTATTCCAGAAGAATTGAGATGGAGCAACTGGGCTCAAGATGATGAA

GGAATTACAGGCGATGAGCTTTTAGACTTTGTAAACAATAAATTATTCAAAGGTTTA

AAGGAAATGGAAGTAGATGAGAATAGTGATGCTAAAGCTTTATTAGTTAAATCTGT

ATTTGAAGATTCCTATAATTATATGAAATCAGGAGCTTTAATGAGGCAGGTAATAAA

TAAGTTAAATGAAATAGATTTTACAGCAGGTGAAGACAGACATTTATTTAATGATAT

ATATGAAAATATATTAAAAGATCTTCAAAGTGCAGGCAATGCAGGAGAATTCTATA

CACCAAGACCTGTTACACAATTTATAATAGATATGCTAAGTCCAAAGCTTGGTGAAA

AAGTAGCTGACTTTGCTTGTGGTACCGGTGGATTTTTAACATGTGCCATAGAAAACT

TAAAAAAACAGGAAACCAAAGTTGAAGATTTAAAAATATTAGGTGAAACCATAATG

GGTGTAGAAAAGAAACCGCTTCCTCACATGCTTGCTACAACTAACCTGATACTTCAT

GATATTGATGTGCCAAACATAAAACATGATAATTCTTTGATGAAGAATGTAAGAGAT

-continued

```
TTAAAGCCTTCAGAATATGTGGATGTAATAGCAATGAATCCTCCTTTTGGCGGAATT

GAAGAAGATATGGTACTAACTAATTTCCCTCAGCAGTTTCAAACAAAAGAAACAGC

AGATTTATTTATGACTCTTATAATGTATAGATTAAGTGAAAAAGGAAGAGCGGGAGT

AGTACTTCCAGATGGATTTTTATTTGGTGAAGGTGTAAAGACTCATATAAAAGAAAA

ACTTTTAAATGAATTTAACCTTCATACTATAGTAAGAATGCCTAATGGAGTATTTGC

CCCATATACGGGAATAAATACAAACCTTTTATTCTTTGAAAAAGGTAAGCCAACAGA

AGAAGTTTGGTTCTTTGAACATCCACTTCCTGAAGGATATAAAAATTATACTAAAAC

CAAACCAATAAGATATGAAGAATTTGAACTGGAGAAGAAGTGGTGGAATAACAGA

GAAGAAAATGAGTATGCGTGGAAGGTTTCAGTAGAGGACATTAAAAATAGAAATTA

TAATTTAGATTATAAAAATCCTAATAAGGAAGAAGAAGATTTAGGAGATCCAAAGG

CATTATTAAAAAAATATCATGAAGCTGCTGCTGATGTAGATAAATTGCAAGATTCTT

TGATAGATGAATTAAAGAAGATTTTAGAAGGGACATCAAAATAG

SEQ ID NO: 7: Pptaack-MTI-12
TGATTGATTATTTATTTTAAAATGCCTAAGTGAAATATATACATATTATAACAATAA

AATAAGTATTAGTGTAGGATTTTTAAATAGAGTATCTATTTTCAGATTAAATTTTTGA

TTATTTGATTTACATTATATAATATTGAGTAAAGTATTGACTAGCAAAATTTTTTGAT

ACTTTAATTTGTGAAATTTCTTATCAAAAGTTATATTTTTGAATAATTTTTATTGAAA

AATACAACTAAAAAGGATTATAGTATAAGTGTGTGTAATTTGTGTTAAATTTAAAG

GGAGGAAAATGAATACACAGGAAATAGTAAGCAAACTTTGGAACCTTTGTAACGTA

CTAAGAGATGATGGAATAACTTATCATCAATATGTAACAGAATTAACATATATTCTT

TTCTTAAAGATGGCAAAGGAAACAGGTACAGAGGATAAATTGCCAGAAGGTTATAG

ATGGGATGATTTAAAAGTTTATAGAGGAATGGAACTTAAGAAATTTTATAATAAATT

ATTAAATTATCTTGGAGAAAAGACTACTGGGATAGTGCAAAAAATATATCAGGGAT

CTGCAACAAATATAGAAGAACCAAAAAATCTAGAAAAAATAATTAAAACTATAGAT

GGATTAGATTGGTATTCAGCAAAAGAAGAAGGACTTGGAAACTTATATGAAGGATT

ACTTGAAAAAAATGCATCTGAGAAAAAATCTGGTGCAGGACAATACTTTACTCCAA

GAGTATTAATTAATGTTATGGTGGAACTTATTGATCCAAAACCAGGTGAAAAATGCA

ATGACCCTGCAGCAGGAACCTTTGGATTTATGATTGCTGCAGATCGTTACATGAAAC

AGAAAACAGACAACTATTTTGATTTAGGTACAGAACTTCAAGAGTTTCAGAGAACT

AAGGCTTTTTCTGGCTGTGAATTAGTTCACGAAACACATAGATTAGCCCTTATGAAT

GCTATGCTTCATGATATAGAAGGAAACATAATCCTCGGAGATACTTTAACAAATACA

GGAAAGCAGATGAAAGACTTAAATGTTGTGCTTTCAAACCCTCCATTTGGAACTAAA

AGAGGTGGTGAAAGAGCAACAAGAGATGATTTGACTTACATGACTTCAAATAAACA

ATTAAACTTCTTGCAGCACATATATAGAAGTTTAAAAGCAGATGGAAAAGCAAGAG

CAGCTGTGGTATTGCCAGATAATGTACTATTTGATCATAATGATGGAGCGAAGATTC

GTGCGGATTTAATGGATAAATGTAATCTACATACAATATTACGGTTACCTACTGGTA

TTTTCTATGCTAAAGGAGTTAAAACAAATGTGCTTTTCTTTACTAGAGGTACTAGTG

ATAAAGACAATACTAAAGAAGTTTGGATATATGATTTGCGTACCAATATGCCTAGCT

TTGGAAAGACAAATCCTTTAAAGAAAGAGCATTTTGAAGACTTTATAAAGGCTTATA

CTTCTGAGGATAGAACAAAGGTGAAAGATGAACGTTTTTCGGTATTTACTAGAGAA

GAAATAAAAGAGAAAAATGATAACCTTGACCTAGGTTTAATTCGTGATGAAAGTGT
```

```
-continued
ATTAGACTATGAAGATCTACAAGATCCAATTGAAAGTGGTGAAGAAATAACTTCAC

AACTTGAAGAGGCAATGGATTTAATCCAAACTGTTGTAAAGAAACTAAAGATTTTA

GGCGGTGACAGGTAATGTCAATAACAAACGTAGTAAAATCAGTACAAGATATAATG

CGCCAGGATGCAGGGGTAGATGGAGATGCTCAAAGAATATCTCAACTAGTTTGGAT

GATATTTTTAAAGGTATTTGATGCAAAAGAAGAGGAATGGGAATTAGAGTATGATG

ATTATACACCTATTATTCCAGAAGAATTGAGATGGAGCAACTGGGCTCAAGATGATG

AAGGAATTACAGGCGATGAGCTTTTAGACTTTGTAAACAATAAATTATTCAAAGGTT

TAAAGGAAATGGAAGTAGATGAGAATAGTGATGCTAAAGCTTTATTAGTTAAATCT

GTATTTGAAGATTCCTATAATTATATGAAATCAGGAGCTTTAATGAGGCAGGTAATA

AATAAGTTAAATGAAATAGATTTTACAGCAGGTGAAGACAGACATTTATTTAATGAT

ATATATGAAAATATATTAAAAGATCTTCAAAGTGCAGGCAATGCAGGAGAATTCTA

TACACCAAGACCTGTTACACAATTTATAATAGATATGCTAAGTCCAAAGCTTGGTGA

AAAAGTAGCTGACTTTGCTTGTGGTACCGGTGGATTTTTAACATGTGCCATAGAAAA

CTTAAAAAAACAGGAAACCAAAGTTGAAGATTTAAAAATATTAGGTGAAACCATAA

TGGGTGTAGAAAAGAAACCGCTTCCTCACATGCTTGCTACAACTAACCTGATACTTC

ATGATATTGATGTGCCAAACATAAAACATGATAATTCTTTGATGAAGAATGTAAGAG

ATTTAAAGCCTTCAGAATATGTGGATGTAATAGCAATGAATCCTCCTTTTGGCGGAA

TTGAAGAAGATATGGTACTAACTAATTTCCCTCAGCAGTTTCAAACAAAAGAAACA

GCAGATTTATTTATGACTCTTATAATGTATAGATTAAGTGAAAAAGGAAGAGCGGG

AGTAGTACTTCCAGATGGATTTTTATTTGGTGAAGGTGTAAAGACTCATATAAAAGA

AAAACTTTTAAATGAATTTAACCTTCATACTATAGTAAGAATGCCTAATGGAGTATT

TGCCCCATATACGGGAATAAATACAAACCTTTTATTCTTTGAAAAAGGTAAGCCAAC

AGAAGAAGTTTGGTTCTTTGAACATCCACTTCCTGAAGGATATAAAAATTATACTAA

AACCAAACCAATAAGATATGAAGAATTTGAACTGGAGAAGAAGTGGTGGAATAACA

GAGAAGAAAATGAGTATGCGTGGAAGGTTTCAGTAGAGGACATTAAAAATAGAAAT

TATAATTTAGATTATAAAAATCCTAATAAGGAAGAAGAAGATTTAGGAGATCCAAA

GGCATTATTAAAAAAATATCATGAAGCTGCTGCTGATGTAGATAAATTGCAAGATTC

TTTGATAGATGAATTAAAGAAGATTTTAGAAGGGACATCAAAATAG
```

SEQ ID NO: 8: Amino acid sequences of MTI-12
```
M N T Q E I V S K L W N L C N V L R D D G I T Y H Q Y V T E L T Y I
L F L K M A K E T G T E D K L P E G Y R W D D L K V Y R G M E L K
K F Y N K L L N Y L G E K T T G I V Q K I Y Q G S A T N I E E P K N
L E K I I K T I D G L D W Y S A K E E G L G N L Y E G L L E K N A S
E K K S G A G Q Y F T P R V L I N V M V E L I D P K P G E K C N D P
A A G T F G F M I A A D R Y M K Q K T D N Y F D L G T E L Q E F Q
R T K A F S G C E L V H E T H R L A L M N A M L H D I E G N I I L G
D T L T N T G K Q M K D L N V V L S N P P F G T K R G G E R A T R
D D L T Y M T S N K Q L N F L Q H I Y R S L K A D G K A R A A V V
L P D N V L F D H N D G A K I R A D L M D K C N L H T I L R L P T G
I F Y A K G V K T N V L F F T R G T S D K D N T K E V W I Y D L R T
N M P S F G K T N P L K K E H F E D F I K A Y T S E D R T K V K D E
```

```
RFSVFTREEIKEKNDNLDLGLIRDESVLDYEDLQ

DPIESGEEITSQLEEAMDLIQTVVKKLKILGGDR

MSITNVVKSVQDIMRQDAGVDGDAQRISQLVWM

IFLKVFDAKEEEWELEYDDYTPIIPEELRWSNWA

QDDEGITGDELLDFVNNKLFKGLKEMEVDENSD

AKALLVKSVFEDSYNYMKSGALMRQVINKLNEI

DFTAGEDRHLFNDIYENILKDLQSAGNAGEFYTP

RPVTQFIIDMLSPKLGEKVADFACGTGGFLTCAI

ENLKKQETKVEDLKILGETIMGVEKKPLPHMLAT

TNLILHDIDVPNIKHDNSLMKNVRDLKPSEYVDV

IAMNPPFGGIEEDMVLTNFPQQFQTKETADLFMT

LIMYRLSEKGRAGVVLPDGFLFGEGVKTHIKEKL

LNEFNLHTIVRMPNGVFAPYTGINTNLLFFEKGK

PTEEVWFFEHPLPEGYKNYTKTKPIRYEEFELEK

KWWNNREENEYAWKVSVEDIKNRNYNLDYKNP

NKEEEDLGDPKALLKKYHEAAADVDKLQDSLID

ELKKILEGTSK
```

SEQ ID NO: 9: Polynucleotide sequence of MTII-1.
```
ATGCATAAGTGGCGTGATTTATCTATACTTGGAGAAATGTATGAAAGATCAATGGAA

AAGGAAGAAAGAAAACGGAAGGGGAGTTTTTATACTCCTCATTACATAGTTGACTA

TATAGTGAAGAATATTATGTCAAATTTAGATCTTAAAAAAAATCCTTTTATAAAAGT

ATTAGATCCTTCTTGTGGAAGTGGATATTTTCTAGTAAGAGTATACGAAATTTTAAT

GGAAAAGTTCAGTCAAAATTTAGAGCACATTAGAAATACTTTTAACGATAAAACTTA

TACCATTGAAACTGAAGATGGATTAAAGAGTATAGACGGATTTCACTATTGGCAGC

AGGAAAATTTAAGCTTTCATATATTAAAGAAATGTATATATGGTGCAGATATAGACA

GCATCGCTGTAGAGCTTACAAAAATTAATTTAAGTAAAGTCAGTGGTATAAACATTA

ATATGGAGGACAATATCATATGCTGCAACAGTCTTATAAAGTGGAATCAAATTGATA

ATGTAGAAAATATAAGGAATCTAATATTCAATCTGTTGTTAAGTTTTGGAACACAA

AATATGATTATGTACTGGGGAATCCTCCTTGGGTATCTTTAAGTCGAAAGAATAAGA

TGAATATAGAGGATGGATTGTTAAAGTATTATAGTGAAAATTATAATGGAAATACAT

ATTTACCTAATTTGTATGAGTATTTTATAAAAAGGTCTATGGAAATATTAAAGCCGG

GAGGAAGATTTGGATTTGTAGTTCCTGATAGGCTGTCACGAAATCTTCAATACAGTG

AACTTAGAAAGAGTTTACTTGAAAATTATAATATATTAAATCTTGTGTTTGAGATAG

ATTTTCCGGAAATAAACACAGATTCTATGATTATGATAGCAGAAAATAAACATAGA

AAAGTAAATAAAATAGAAATAGATATTTATAAGAAGAGGACATATGAAATGTATCA

GCATGAATATCTGAGAAATTCAAAATTTAAGTTTACATATTGTTGTTATAATCAAAA

CTTAAGCATAAAGGATTGTATAGAGAAAAATAGCAGCAAATTAAAAAGCATTTCCA

AGACTTTTACAGGATTTATAGGTTATAGTAAAAAAATAACTCCTGTTAAAAAAAATC

AACATCAGGTTGAAGTATTAAAAGGGGAAAATATAAAAAAGTTTCGAGTTTTAAAC

AATTACTATTATGATTTTGTGCCTGAAAACATAATAGGCGGAACTAAAAATATAGAA

AAACTTACTTTTAAAAATAAATTAGTAATAAGGAAAACTGGAAAAAATTTAATAGC
```

-continued
AGCTTTAGATGATAAGGGACGTATAATAGAACAATCTCTATATGGAATAATAAGTA

CAAATGAGGAATTTTCACCTCAGTATATTTTGGCAATATTGAATTCAGAGTTAATTC

AATGGTATTATTTAAATTTTTTAATTACCAACTCTAATTCTATTCCACAAATTAAAAA

ATGCAATTTGGATGAAATACCAATAAGACATTGCAGCAGACAAGCTAAAGAAGACA

TAGAAAAATTAGTTTGCAAAATTATAAATGATAATGATCAAAAAAATATGTTGAAG

AAAATATTAGATGATGAGATATTTGAATTATATAATATTGATCATAATTATAGAAGA

ATTATATTAAATGATATTGAAAATAA

SEQ ID NO: 10: Amino acid sequence of MTII-1.
M H K W R D L S I L G E M Y E R S M E K E E R K R K G S F Y T P H

Y I V D Y I V K N I M S N L D L K K N P F I K V L D P S C G S G Y F

L V R V Y E I L M E K F S Q N L E H I R N T F N D K T Y T I E T E D

G L K S I D G F H Y W Q Q E N L S F H I L K K C I Y G A D I D S I A

V E L T K I N L S K V S G I N I N M E D N I I C C N S L I K W N Q I D

N V E K Y K E S N I Q S V V K F W N T K Y D Y V L G N P P W V S L

S R K N K M N I E D G L L K Y Y S E N Y N G N T Y L P N L Y E Y F I

K R S M E I L K P G G R F G F V V P D R L S R N L Q Y S E L R K S L

L E N Y N I L N L V F E I D F P E I N T D S M I M I A E N K H R K V

N K I E I D I Y K K R T Y E M Y Q H E Y L R N S K F K F T Y C C Y N

Q N L S I K D C I E K N S S K L K S I S K T F T G F I G Y S K K I T P

V K K N Q H Q V E V L K G E N I K K F R V L N N Y Y Y D F V P E N

I I G G T K N I E K L T F K N K L V I R K T G K N L I A A L D D K G

R I I E Q S L Y G I I S T N E E F S P Q Y I L A I L N S E L I Q W Y Y L

N F L I T N S N S I P Q I K K C N L D E I P I R H C S R Q A K E D I E

K L V C K I I N D N D Q K N M L K K I L D D E I F E L Y N I D H N Y

R R I I L N D I E N *

SEQ ID NO: 11: Ppta-ack-MTII-1.
TGCCTAAGTGAAATATATACATATTATAACAATAAAATAAGTATTAGTGTAGGATTT

TTAAATAGAGTATCTATTTTCAGATTAAATTTTTGATTATTTGATTTACATTATATAA

TATTGAGTAAAGTATTGACTAGCAAAATTTTTTGATACTTTAATTTGTGAAATTTCTT

ATCAAAAGTTATATTTTTGAATAATTTTTATTGAAAAATACAACTAAAAAGGATTAT

AGTATAAGTGTGTGTAATTTTGTGTTAAATTTAAAGGGAGGAAA

ATGCATAAGTGGCGTGATTTATCTATACTTGGAGAAATGTATGAAAGATCAATGGAA

AAGGAAGAAAGAAAACGGAAGGGGAGTTTTTATACTCCTCATTACATAGTTGACTA

TATAGTGAAGAATATTATGTCAAATTTAGATCTTAAAAAAAATCCTTTTATAAAAGT

ATTAGATCCTTCTTGTGGAAGTGGATATTTTCTAGTAAGAGTATACGAAATTTTAAT

GGAAAAGTTCAGTCAAAATTTAGAGCACATTAGAAATACTTTTAACGATAAAACTTA

TACCATTGAAACTGAAGATGGATTAAAGAGTATAGACGGATTTCACTATTGGCAGC

AGGAAAATTTAAGCTTTCATATATTAAAGAAATGTATATATGGTGCAGATATAGACA

GCATCGCTGTAGAGCTTACAAAAATTAATTTAAGTAAAGTCAGTGGTATAAACATTA

ATATGGAGGACAATATCATATGCTGCAACAGTCTTATAAAGTGGAATCAAATTGATA

ATGTAGAAAAATATAAGGAATCTAATATTCAATCTGTTGTTAAGTTTTGGAACACAA

AATATGATTATGTACTGGGGAATCCTCCTTGGGTATCTTTAAGTCGAAAGAATAAGA

-continued

```
TGAATATAGAGGATGGATTGTTAAAGTATTATAGTGAAAATTATAATGGAAATACAT

ATTTACCTAATTTGTATGAGTATTTTATAAAAAGGTCTATGGAAATATTAAAGCCGG

GAGGAAGATTTGGATTTGTAGTTCCTGATAGGCTGTCACGAAATCTTCAATACAGTG

AACTTAGAAAGAGTTTACTTGAAAATTATAATATATTAAATCTTGTGTTTGAGATAG

ATTTTCCGGAAATAAACACAGATTCTATGATTATGATAGCAGAAAATAAACATAGA

AAAGTAAATAAAATAGAAATAGATATTTATAAGAAGAGGACATATGAAATGTATCA

GCATGAATATCTGAGAAATTCAAAATTTAAGTTTACATATTGTTGTTATAATCAAAA

CTTAAGCATAAAGGATTGTATAGAGAAAAATAGCAGCAAATTAAAAAGCATTTCCA

AGACTTTTACAGGATTTATAGGTTATAGTAAAAAAATAACTCCTGTTAAAAAAAATC

AACATCAGGTTGAAGTATTAAAAGGGGAAAATATAAAAAAGTTTCGAGTTTTAAAC

AATTACTATTATGATTTTGTGCCTGAAAACATAATAGGCGGAACTAAAAATATAGAA

AAACTTACTTTTAAAAATAAATTAGTAATAAGGAAAACTGGAAAAAATTTAATAGC

AGCTTTAGATGATAAGGGACGTATAATAGAACAATCTCTATATGGAATAATAAGTA

CAAATGAGGAATTTTCACCTCAGTATATTTTGGCAATATTGAATTCAGAGTTAATTC

AATGGTATTATTTAAATTTTTTAATTACCAACTCTAATTCTATTCCACAAATTAAAAA

ATGCAATTTGGATGAAATACCAATAAGACATTGCAGCAGACAAGCTAAAGAAGACA

TAGAAAAATTAGTTTGCAAAATTATAAATGATAATGATCAAAAAAATATGTTGAAG

AAAATATTAGATGATGAGATATTTGAATTATATAATATTGATCATAATTATAGAAGA

ATTATATTAAATGATATTGAAAATAA
```

The invention claimed is:

1. A method of generating a bacterial recombinant cell expressing a DNA Type I methyltransferase having biological activities, comprising:
   (a) introducing a methylation vector into a bacterial host cell wherein said methylation vector expresses a DNA Type I methyltransferase polynucleotide, wherein the DNA Type I methyltransferase polynucleotide is selected from the group consisting of a polynucleotide comprising a nucleotide sequence having at least 98% sequence identity with SEQ ID NO: 1, a polynucleotide encoding a polypeptide having an amino acid sequence at least 97% sequence identity with the polypeptide SEQ ID NO: 2, a polynucleotide comprising a nucleotide sequence having at least 97% sequence identity with SEQ ID NO: 3, and a polynucleotide encoding a polypeptide having an amino acid sequence at least 98% sequence identity with the polypeptide of SEQ ID NO: 4;
   (b) introducing a transforming vector into the bacterial host cell wherein said transforming vector comprises plasmid DNA that is methylated by said methylation vector; and
   (c) purifying and transferring the methylated plasmid DNA from the bacterial host cell to a second bacterial recipient cell that can degrade the plasmid DNA but which cannot degrade the methylated DNA.

2. The method of claim 1 wherein the DNA Type I methyltransferase polynucleotide is expressed from an operably-linked promoter.

3. The method of claim 2 wherein the operably-linked promoter is phosphotransacetylase-acetate kinase operon.

4. The method of claim 1 wherein the bacterial host cell is *Escherichia coli*.

5. The method of claim 1 wherein the second bacterial recipient cell is *Clostridia*.

6. The method of claim 1 wherein the methylated plasmid DNA is transferred from the bacterial host cell to a second bacterial recipient cell by transformation.

7. The method of claim 6 wherein transformation is electroporation or conjugation.

8. The method of claim 1 further comprising isolating stable bacterial transformants containing the methylated plasmid DNA.

9. The method of claim 1 further comprising introducing a shuttle vector into the bacterial host cell.

10. The method of claim 9 wherein the shuttle vector is pACR-1.

11. The method of claim 1 further comprising introducing a conjugation vector into the bacterial host cell.

12. The method of claim 11 wherein the conjugation vector is pACC-1.

* * * * *